US 7,714,032 B2

(12) United States Patent
Kamata et al.

(10) Patent No.: US 7,714,032 B2
(45) Date of Patent: May 11, 2010

(54) THIOL COMPOUND AND PHOTOSENSITIVE COMPOSITION USING THE SAME

(75) Inventors: Hirotoshi Kamata, Kanagawa (JP); Mina Onishi, Kanagawa (JP); Katsumi Murofushi, Kanagawa (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 12/179,727

(22) Filed: Jul. 25, 2008

(65) Prior Publication Data

US 2008/0286690 A1      Nov. 20, 2008

Related U.S. Application Data

(62) Division of application No. 11/666,223, filed as application No. PCT/JP2005/019959 on Oct. 25, 2005.

(60) Provisional application No. 60/624,529, filed on Nov. 4, 2004, provisional application No. 60/624,548, filed on Nov. 4, 2004.

(30) Foreign Application Priority Data

Oct. 26, 2004   (JP)   ............................. 2004-311234
Oct. 26, 2004   (JP)   ............................. 2004-311276

(51) Int. Cl.
*A61L 27/34*      (2006.01)
*C08G 59/42*      (2006.01)

(52) U.S. Cl. ............................... 522/49; 522/6; 522/51; 522/57; 568/67

(58) Field of Classification Search ...................... 522/6, 522/49, 57, 51; 568/67
See application file for complete search history.

(56) References Cited

U.S. PATENT DOCUMENTS 6,551,710 B1 *   4/2003   Chen et al. .................. 428/412

FOREIGN PATENT DOCUMENTS

| EP | 0 987 567 A1 | 3/2000 |
|---|---|---|
| EP | 1 057 808 A2 | 12/2000 |
| JP | 8-59775 A | 3/1996 |
| JP | 10-253815 A | 9/1998 |
| JP | 10-253816 A | 9/1998 |
| JP | 10-253817 A | 9/1998 |
| JP | 2000-249822 A | 9/2000 |
| JP | 2004-149755 A | 5/2004 |
| WO | WO 2004055597 A1 * | 7/2004 |

OTHER PUBLICATIONS

Mitsuaki Yamada et al., "Synthesis of Fluorenebisphenoxy Derivatives by Acid-sulfur Compound Catalyzed Condensation Reaction", Chemistry Letters, vol. 10, 1998, p. 1055-1056.
English language machine translation of JP 08-059775.

* cited by examiner

*Primary Examiner*—Mark Eashoo
*Assistant Examiner*—Jessica Paul
(74) *Attorney, Agent, or Firm*—Sughrue Mion, PLLC

(57) ABSTRACT

The present invention relates to a thiol compound represented by formula (1): wherein $R^1$, $R^2$ and n have the same meanings as in the specification, method for producing the compound, and to a photosensitive composition and a black matrix resist composition using the same which have high sensitivity and excellent property of retaining a line width in fine line patterns at the time of alkaline development, that is, being excellent in development latitude.

(1)

$$HS-R^2-\underset{O}{\overset{\|}{C}}-(O-R^1)_n-O-\bigcirc-\bigcirc-O-(R^1-O)_n-\underset{O}{\overset{\|}{C}}-R^2-SH$$

15 Claims, 4 Drawing Sheets

```
*1:7.747    *4:7.111    *7:4.117    *9:2.660    *10:2.350
   7.729       7.089       4.105       2.645    *11:2.039
*2:7.363    *5:6.751       4.094       2.620    *12:1.834
   7.344       6.730    *8:3.384       2.606        1.817
   7.333    *6:4.421       3.367       2.587    *13:1.565
   7.315       4.410       3.349       2.566    *14:1.363
*3:7.267       4.398       3.332       2.547        1.346
   7.249                   3.315                 *15 0.000
   7.231
```

| *1:170.937 | *7 :127.619 | *12:65.781 |
| *2:157.036 | 127.305 | *13:64.156 |
| *3:151.517 | *8 :125.878 | *14:62.910 |
| *4:139.844 | *9 :120.087 | *15:45.701 |
| *5:138.566 | *10:114.172 | *16:31.248 |
| *6:129.137 | *11: 77.313 | *17:24.814 |
|  | 77.000 |  |
|  | 76.687 |  |

| *1:7.746 | *5:7.247 | *9:4.146 |
| 7.728 | 7.230 | 4.135 |
| *2:7.360 | *6:7.112 | 4.124 |
| 7.342 | 7.090 | *10:2.423 |
| 7.333 | *7:6.760 | *11:1.552 |
| *3:7.314 | 6.739 | *12:1.525 |
| *4:7.266 | *8:4.432 | |
| | 4.422 | |
| | 4.410 | |

| *1:175.054 | *7 :127.875 | *12: 65.996 |
| *2:157.416 |    127.562  | *13: 64.420 |
| *3:151.782 | *8 :126.143 |      64.082 |
| *4:140.109 | *9 :120.343 | *14: 45.075 |
| *5:138.839 | *10:114.585 | *15: 29.195 |
| *6:129.401 | *11: 77.578 |             |
|            |      77.265 |             |
|            |      76.943 |             |

THIOL COMPOUND AND PHOTOSENSITIVE COMPOSITION USING THE SAME

CROSS REFERENCE TO RELATED APPLICATIONS

This is a divisional of application Ser. No. 11/666,223 filed Apr. 25, 2007, which is a 371 of PCT/JP2005/019959 filed Oct. 25, 2005, which claims priority under 35 USC 119 from Japanese Patent Application Nos. 2004-311234 and 2004-311276 and claims the benefit of U.S. Provisional Application Ser. No. 60/624,529 filed Nov. 4, 2004, and No. 60/624,548 filed Nov. 4, 2004, the disclosures of all of which are incorporated by reference herein.

TECHNICAL FIELD

The present invention relates to a novel thiol compound having a fluorene skeleton, a method for producing the same, and to an alkali developable type photosensitive composition and a black matrix resist composition for a color filter using the compound. More specifically, the present invention relates to a novel thiol compound having a fluorene skeleton, and to a photosensitive composition and a black matrix resist composition for a color filter with high sensitivity and excellent property of retaining a line width in fine line patterns at the time of alkaline development, containing: (A) a photopolymerization initiator system including the compound; (B) a binder resin having a carboxyl group; and (C) a compound having an ethylenically unsaturated group.

BACKGROUND ART

Photosensitive compositions are used in various fields including printing plates, color proofs, color filters, solder resists and photo-curing ink. In particular, in recent years, curing at room temperature, fast-curing and solvent absence, which are the most characteristic properties of photo-curing, have received attention in various fields including those applications from the viewpoints of environmental concerns, energy saving, safety in working, production costs and the like and many studies and developments have been made on photosensitive compositions.

Photosensitive compositions are each mainly composed of a photopolymerization initiator, a binder resin, a compound having an ethylenically unsaturated bond which cures by a polymerization reaction, and various kinds of additives, and the kinds of the components depend on use to which the photosensitive composition is applied.

The compounds which constitute the photopolymerization initiator are selected by their photosensitive wavelengths and polymerization initiating properties. The binder resin, the compound having an ethylenically unsaturated bond, and the additives are selected by polymerizability and physical properties of a desired cured product. They are used for a photosensitive composition in combinations.

However, some binder resins, some compounds each having an ethylenically unsaturated bond, and some additives occasionally cause problems as follows in the photosensitive compositions. (1) Sufficient energy for initiating photopolymerization is not obtained; (2) preservation stability is not obtained; (3) since irradiation light does not reach deep enough in a desired cured product owing to the thickness thereof, curing does not proceed sufficiently; (4) oxygen inhibition occurs at the portion where the photosensitive composition contacts the air; and (5) property of retaining a line width of fine line patterns at alkaline development is inferior.

For those problems, various measures have been taken; for example, irradiation with greater light energy, use of an excess amount of a photopolymerization initiator, and placement of an oxygen shielding membrane. Also for energy saving and reduction in production cost, a photosensitive composition having more excellent photosensitivity is desired.

Of those, in the development of color filters to be used for color televisions, liquid crystal display devices, solid-state image sensing devices, cameras and the like, pigment-dispersing resists for color filters have been studied for an improvement in productivity and high definition. In such applications, there have been growing demands on photosensitive compositions such as one to be cured at lower energy, one to be cured more quickly, one capable of forming finer patterns, and one having a greater depth of curing.

A color filter is usually manufactured by forming a lattice-like black-colored matrix (black matrix) on the surface of a transparent substrate such as glass or a plastic sheet and then forming three or more different hue patterns of red, green, blue and the like to an accuracy of several micrometers. Of those, the black matrix is arranged for improving contrast and preventing malfunction of TFT. Though a resist for forming the black matrix (black matrix resist) has a high light-blocking effect and thus can be hardly photo-cured by nature, high sensitivity has become demanded with growth in the size of a glass substrate to be used. At the same time, the black matrix resist with which no substantial change in line width of fine line patterns occurs even after being exposed to an alkaline developer for a long time, i.e., one having an excellent development latitude has been demanded strongly.

In late years, liquid crystal displays have come into use for television sets and thus demands have risen for color filters having excellent chromatic contrasts. In addition, there is a demand for a pigment in a concentrated amount but it may lead to less sensitivity. Therefore, for improving the sensitivity of the photosensitive composition and a black matrix resist composition for a color filter, the use of polyfunctional thiol compounds has been proposed (JP 10-253815 A, JP 10-253816 A, JP 10-253817 A, JP 2004-149755, etc.).

However, polyfunctional thiol compounds, which have been proposed heretofore, have aliphatic polyol components provided as their basic skeletons, so that photo-cured products thereof might cause a problem of smaller line widths of fine line patterns due to their inferior alkali-resistant development properties, although the sensitivity of the composition can be enhanced. In other words, there has been a problem of insufficient development latitude. In particular, for the black matrix resist on which lattice-like patterns should be formed, a phenomenon in which the line width of fine line patterns becomes small has become a very critical problem.

DISCLOSURE OF THE INVENTION

An object of the present invention is to provide a high-sensitive photosensitive composition and a black matrix resist composition excellent in property of retaining a line width in fine line patterns at the time of alkaline development, i.e., development latitude.

As a result of concentrated study, the inventors of the present invention have completed the present invention by finding out that the above problems can be solved by a photosensitive composition and a black matrix resist composition using a novel thiol compound having a fluorene skeleton.

That is, the present invention pertains to a novel thiol compound according to any one of 1 to 13 described below, a production method thereof, and a photosensitive composition and a black matrix resist composition using the compound.

1. A thiol compound represented by formula (1):

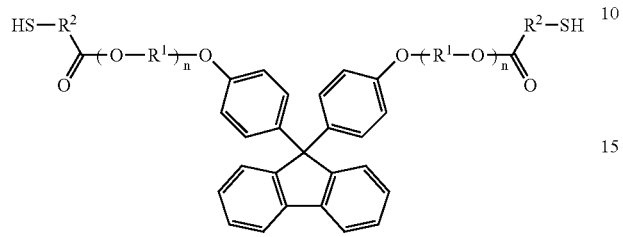

(1)

wherein $R^1$ represents a linear- or branched-chain alkylene group having 2 to 6 carbon atoms, $R^2$ represents a linear- or branched-chain alkylene group having 1 to 6 carbon atoms, and n represents an integer of 1 to 4.

2. The thiol compound according to 1 above, in which $R^1$ is an alkylene group represented by any one of the following formulae (2) to (4).

(2)

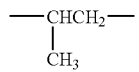

(3)

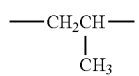

(4)

3. The thiol compound according to 1 above, in which $R^2$ is an alkylene group represented by any one of the following formulae (5) to (9):

(5)

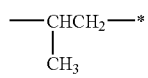

(6)

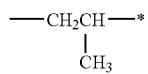

(7)

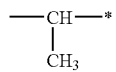

(8)

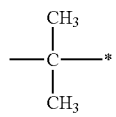

(9)

(* represents a binding site with a mercapto group).

4. The thiol compound according to 1 above, which is represented by the following formula (10).

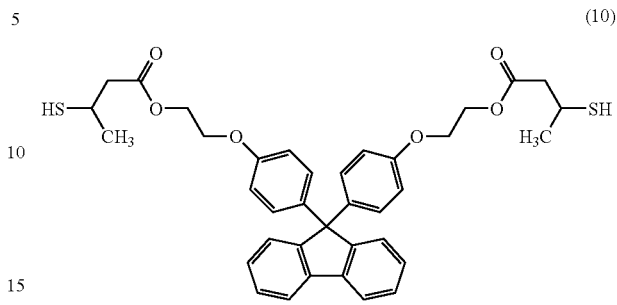

(10)

5. The thiol compound according to 1 above, which is represented by the following formula (11).

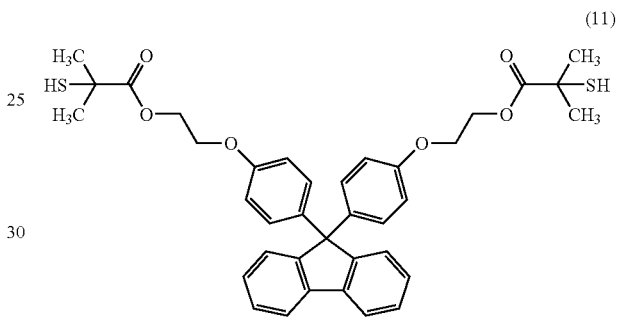

(11)

6. The thiol compound according to 1 above, which is a compound obtained by an esterification reaction between a diol compound represented by the following formula (12):

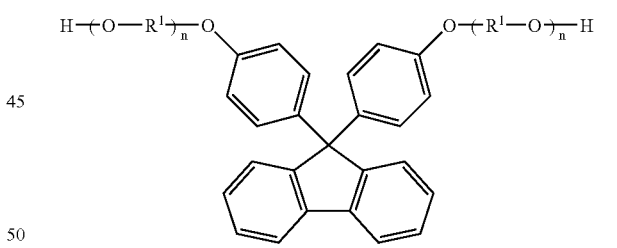

(12)

wherein $R^1$ represents a linear- or branched-chain alkylene group having 2 to 6 carbon atoms and n is an integer of 1 to 4, and a mercapto group-containing carboxylic acid compound represented by the following formula (13):

(13)

wherein $R^2$ represents a linear- or branched-chain alkylene group having 1 to 6 carbon atoms.

7. A method of producing a thiol compound represented by the following formula (1):

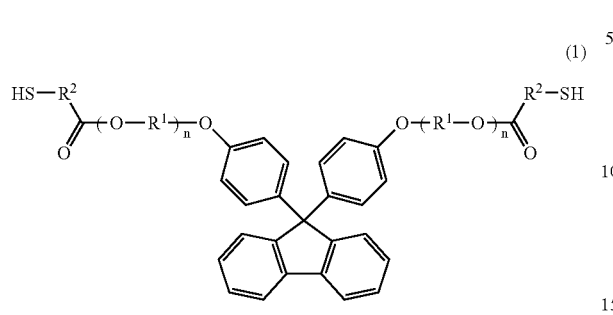

wherein all symbols represent the same meanings as those described above, respectively), characterized by subjecting a diol compound represented by the following formula (12):

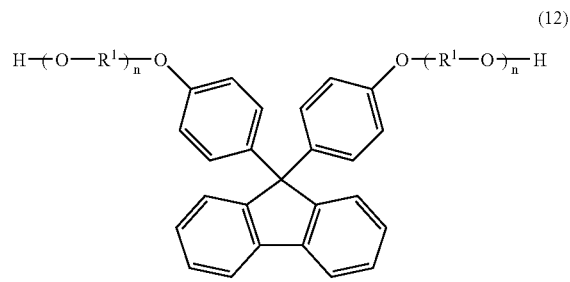

wherein $R^1$ represents a straight- or branched-chain alkylene group having 2 to 6 carbon atoms and n is an integer of 1 to 4, to an esterification reaction with a mercapto group-containing carboxylic acid compound represented by the following formula (13):

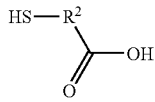

wherein $R^2$ represents a linear- or branched-chain alkylene group having 1 to 6 carbon atoms.

8. A photosensitive composition comprising: (A) a photopolymerization initiator system containing the thiol compound according to any one of 1 to 6 above; (B) a binder resin containing a carboxyl group; and (C) a compound having an ethylenically unsaturated group.

9. The photosensitive composition according to 8 above, in which the photopolymerization initiator system (A) contains a hexaarylbiimidazole compound and/or an aminoacetophenone compound.

10. The photosensitive composition according to 9 above, in which the hexaarylbiimidazole compound is represented by the following formula (14):

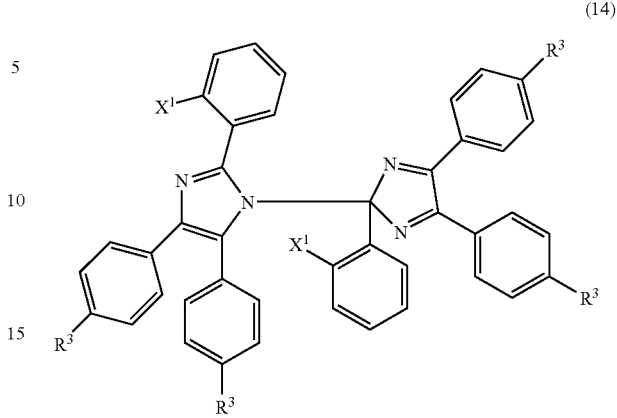

wherein $X^1$ represents a halogen atom and $R^3$ represents an alkyl group or an alkoxy group, which may have a substituent.

11. The photosensitive composition according to 8 above, in which the photopolymerization initiator system (A) contains a sensitizer.

12. The photosensitive composition according to 11 above, in which the sensitizer is one or more compounds selected from the group consisting of benzophenone-based compounds, thioxanthone-based compounds and ketocoumarin-based compounds.

13. The photosensitive composition according to 8 above, in which the binder resin containing a carboxyl group (B) further contains an ethylenically unsaturated group.

14. A black matrix resist composition for a color filter characterized by comprising: (A) a photopolymerization initiator system containing a thiol compound represented by formula (1):

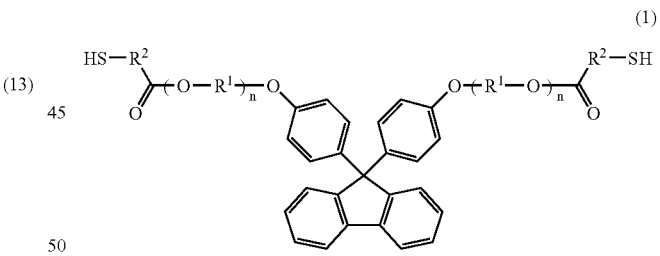

wherein $R^1$ represents a linear- or branched-chain alkylene group having 2 to 6 carbon atoms, $R^2$ represents a linear- or branched-chain alkylene group having 1 to 6 carbon atoms, and n represents an integer of 1 to 4; (B) a binder resin having a carboxyl group; (C) a compound having an ethylenically unsaturated group; (D) a black pigment; and (E) an organic solvent.

15. The black matrix resist composition for a color filter according to 1 above, in which the binder resin (B) having a carboxyl group further contains an ethylenically unsaturated group.

16. The black matrix resist composition for a color filter according to 5 above, in which the binder resin (B) having a carboxyl group is a bisphenol-type epoxyacrylate resin.

17. The black matrix resist composition for a color filter according to 1 above, in which the photopolymerization initiator system (A) contains a hexaarylbiimidazole compound and/or an aminoacetophenone compound.

18. The black matrix resist composition for a color filter according to 17 above, in which the hexaarylbiimidazole compound is a compound represented by formula (14):

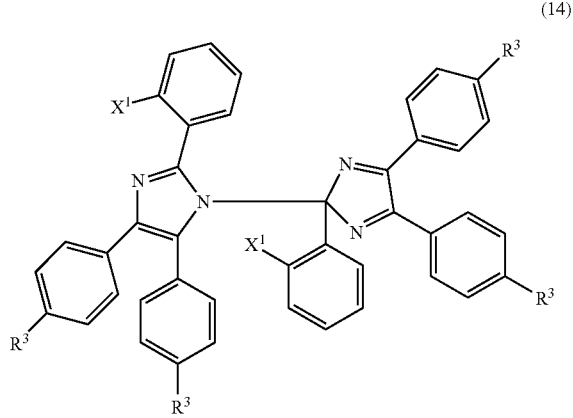

(14)

wherein $X^1$ represents a halogen atom, $R^3$ represents an alkyl group which may have a substituent or an alkoxy group which may have a substituent.

19. The black matrix resist composition for a color filter according to 17 or 18 above, in which the photopolymerization initiator system (A) further contains, as a sensitizer, one or more of compounds selected from the group consisting of a benzophenone-based compound, a thioxanthone-based compound, and a ketocoumarin-based compound.

20. The black matrix resist composition for a color filter according to 14 above, in which the black pigment (D) is carbon black and/or titanium black.

21. The black matrix resist composition for a color filter according to 14 above, in which each of the components except the organic solvent (E) is contained at a rate of content to the total mass of the respective components as follows:
(A) a photopolymerization initiator system: 2 to 15% mass,
(B) a binder resin having a carboxyl group: 10 to 30% by mass,
(C) a compound having an ethylenically unsaturated group: 2 to 20% by mass, and
(D) a black pigment: 40 to 80% by mass.

BEST MODE FOR CARRYING OUT THE INVENTION

1. Thiol Compound having a Fluorene Skeleton

The thiol compound to be used in the present invention is a thiol compound having a fluorene skeleton in a molecule which is represented by formula (1):

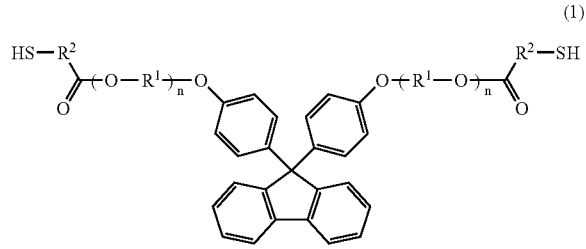

(1)

wherein $R^1$ represents a linear- or branched-chain alkylene group having 2 to 6 carbon atoms, $R^2$ represents a linear- or branched-chain alkylene group having 1 to 6 carbon atoms, and n represents an integer of 1 to 4. When the radical polymerization of the thiol compound is carried out, a radical polymerization inhibition with oxygen can be remarkably decreased and thus a photosensitive composition may show a remarkable increase in photosensitivity. Furthermore, as the thiol compound according to the present invention contains the fluorene skeleton having high hydrophobic property, when the thiol compound is exposed and cured, such hydrophobic property will impart a high alkali resistant development function to a cured product even if the cure extent of the thiol compound is small to some extent.

In formula (1), $R^1$ is preferably a linear- or branched-chain alkylene group having 2 to 6 carbon atoms. If the number of carbon atoms exceeds 6, the development latitude decreases as the hydrophobic property of the molecule itself decreases. More preferable is an alkylene group having a structure represented by any one of formulae (2) to (4).

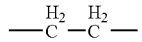

(2)

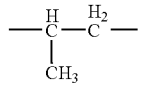

(3)

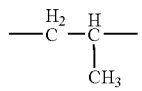

(4)

$R^2$ is preferably a linear- or branched-chain alkylene group having 1 to 6 carbon atoms. If the number of carbon atoms exceeds 6, the development latitude decreases as the hydrophobic property of the molecule itself decreases. $R^2$ is more preferably an alkylene group having a structure represented by any one of formulae (5) to (9):

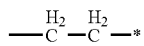

(5)

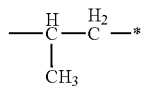

(6)

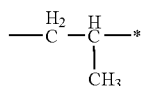

(7)

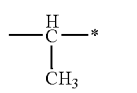

(8)

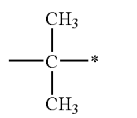

(9)

wherein * represents a binding site with a mercapto group. In consideration of the preservation stability of the composition, the thiol compound having an alkylene group with any one of the structures represented by formulae (7) to (9), which is a secondary or tertiary mercapto group, is particularly preferable.

In formula (1), n is preferably an integer of 1 to 4, more preferably an integer of 1 or 2. If the value of n exceeds 4, the development latitude decreases as the hydrophobic property of the molecule itself decreases.

In addition, the thiol compound of the present invention represented by formula (1) is preferably a polyfunctional thiol compound for imparting high sensitivity to a photosensitive composition and a black matrix resist composition containing such a thiol compound. Therefore, alcohols that react with mercapto group-containing carboxylic acids each represented by the following formula (13):

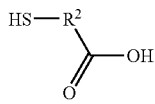
(13)

wherein R² represents a linear- or branched-chain alkylene group having 1 to 6 carbon atoms, thereby to form esters are more desirably diols each represented by the following formula (12), that is, alcohols having fluorene skeletons each containing two alcoholic hydroxyl groups in one molecule:

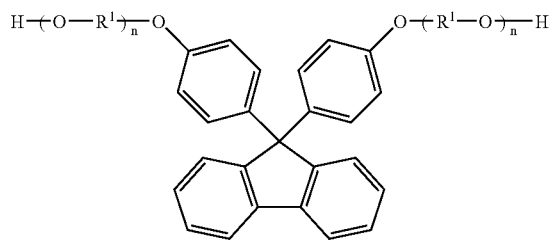
(12)

wherein R¹ represents a linear- or branched-chain alkylene group having 2 to 6 carbon atoms and n represents an integer of 1 to 4.

Specific examples of the diol compound represented by formula (12) include those represented by the following formulae (15) to (18).

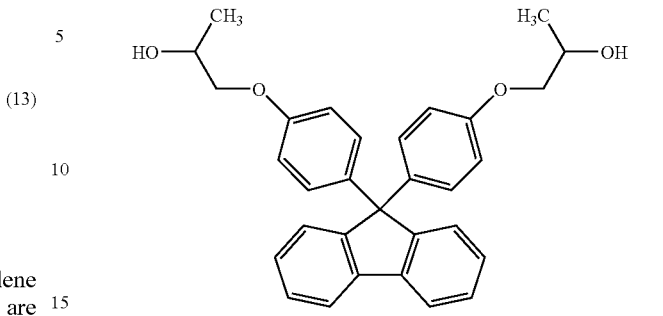
(17)

(18)

On the other hand, examples of the mercapto group-containing carboxylic acid represented by formula (13) include thioglycol acid, 3-mercapto propionic acid, 2-mercapto propionic acid, 3-mercapto butyric acid, and 2-mercapto isobutyric acid. In view of the preservation stability of the photosensitive composition, 2-mercapto propionic acid, 3-mercapto butyric acid and 2-mercapto isobutyric acid each of which forms secondary or tertiary thiol are particularly preferable mercapto group-containing carboxylic acids.

Particularly preferable examples of the thiol compound in the present invention include compounds represented by the following formulae (10) and (11).

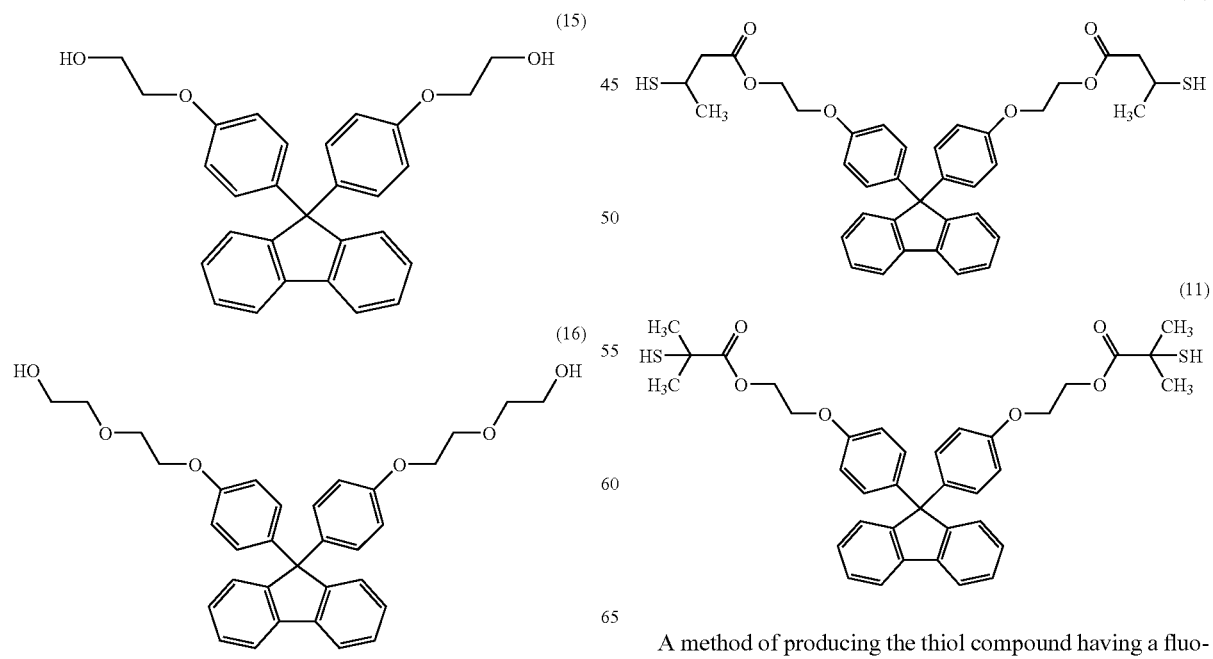
(15)

(16)

(10)

(11)

A method of producing the thiol compound having a fluorene skeleton of the present invention, which is represented by formula (1), is not particularly limited but the thiol compound may be obtained by an esterification reaction between a mercapto group-containing carboxylic acid represented by formula (13) and a diol having a fluorene skeleton represented by formula (12). The esterification reaction itself is well known and the thiol compound can be thus obtained by carrying out the reaction by the conventional method to form ester. The conditions of the esterification reaction are not particularly limited and the conventional reaction conditions may be suitably selected.

In addition, the thiol compound of formula (1) having a fluorene skeleton may be used together with any other thiol compound as far as the development latitude is not affected.

2. Photosensitive Composition and Black Matrix Resist Composition

The photosensitive composition and a black matrix resist composition of the present invention contains, as essential components, (A) a photopolymerization initiator system containing the thiol compound represented by formula (1), (B) a binder resin having a carboxyl group, and (C) a compound having an ethylenically unsaturated bond and may optionally contain any of various additives including pigments and solvents.

2-1. Photopolymerization Initiator System (A)

The photopolymerization initiator system (A) used in the photosensitive composition of the present invention may adopt components other than the above thiol compound having a fluorene skeleton, which are those to be commonly used in the general photopolymerization initiator systems, e.g., radical generators and sensitizers.

(1) Photo-radical Generator

A photo-radical generator to be used in the black matrix resist composition of the present invention can be any one of those known in the art including acetophenone-based compounds, triazine-based compounds, titanocene-based compounds and ketoxime-based compounds. In view of photosensitivity, biimidazole-based compounds and/or aminoacetophenone-based compounds can be preferably used.

(1-1) Biimidazole-based Compound and/or Acetophenone-based Compound

Any one of those commonly used in the ordinary photopolymerization initiator system may be used as a biimidazole-based compound used in the present invention but a hexaarylbiimidazole compound having a structure represented by the following formula (19) is preferable.

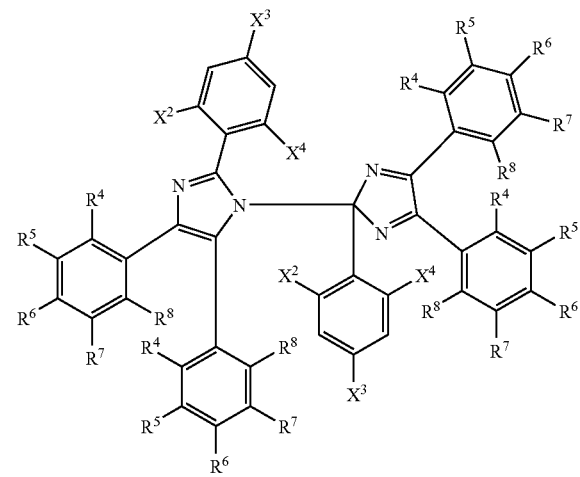

(19)

In formula (19), $X^2$, $X^3$ and $X^4$ represent each independently a halogen atom, a cyano group or a nitro group, $R^4$, $R^5$, $R^6$, $R^7$ and $R^8$ represent each independently a hydrogen atom, an alkyl group which may have a substituent, or an alkoxy group which may have a substituent.

Examples of the halogen atoms represented by the above $X^2$, $X^3$ and $X^4$ include a chlorine atom, a bromine atom and a fluorine atom.

Examples of the alkyl groups represented by the above $R^4$, $R^5$, $R^6$, $R^7$ and $R^8$ include a methyl group, an ethyl group, an n-propyl group, an isopropyl group, an n-butyl group, an isobutyl group, a tert-butyl group, an n-pentyl group and an n-hexyl group. They may have substituents such as an alkoxy group and a halogen atom. Of those, preferable is a linear- or branched-chain alkyl group having 1 to 6 carbons and more preferable is a linear- or branched-chain alkyl group having 1 to 3 carbons.

Examples of the alkoxy groups represented by the above $R^4$, $R^5$, $R^6$, $R^7$ and $R^8$ include a methoxy group, an ethoxy group, a propoxy group, an n-butoxy group, an isobutoxy group, a tert-butoxy group, an n-pentyloxy group, and an n-hexyloxy group. They may have substituents such as an alkoxy group and a halogen atom. Of those, preferable is a linear- or branched-chain alkoxy group having 1 to 6 carbons and more preferable is a linear- or branched-chain alkoxy group having 1 to 3 carbons.

Of those hexaarylbiimidazole compounds, a compound having a structure represented by the following formula (14) is particularly preferable.

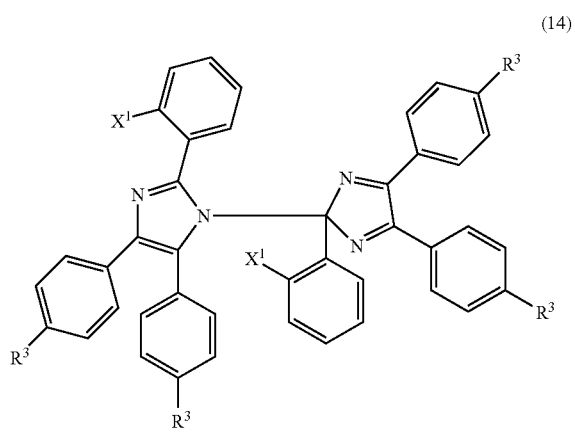

(14)

In the formula, $X^1$ represents a halogen atom and $R^3$ represents an alkyl group which may have a substituent or an alkoxy group which may have a substituent.

Specific examples of the alkyl and alkoxy groups of $R^3$ include the same groups as those listed for $R^4$ to $R^8$ of the hexaarylbiimidazole compound represented by the above formula (19) but a methyl group or a methoxy group is particularly preferable. A chlorine atom is particularly preferable as a halogen atom represented by the above $X^1$.

Examples of an acetophenone-based compound used in the present invention include hydroxyacetophenone compounds and aminoacetophenone compounds. Of those, in terms of photosensitivity, aminoacetophenone compounds are particularly preferable.

Specific examples of the hydroxyacetophenone compound include α-hydroxyacetophenones such as 2-hydroxy-2-methyl-1-phenylpropan-1-one, 2-hydroxy-2-methyl-1-phenylbutan-1-one, 1-(4-methylphenyl)-2-hydroxy-2-methylpropan-1-one, 1-(4-isopropylphenyl)-2-methylpropan-1-one, 1-(4-butylphenyl)-2-hydroxy-2-methylpropan-1-one, 2-hydroxy-2-methyl-1-(4-octylphenyl)propan-1-one, 1-(4-dodecylphenyl)-2-methylpropan-1-one, 1-(4-methoxyphenyl)-2-methylpropan-1-one, 1-(4-methylthiophenyl)-2-methylpropan-1-one, 1-(4-chlorophenyl)-2-hydroxy-2-methylpropan-1-one, 1-(4-bromophenyl)-2-hydroxy-2-methylpropan-1-one, 2-hydroxy-1-(4-hydroxyphenyl)-2-methylpropan-1-one, 1-(4-dimethylaminophenyl)-2-hydroxy-2-methylpropan-1-one, 1-(4-carbethoxyphenyl)-2-hydroxy-2-methylpropan-1-one, 1-hydroxycyclohexylphenyl ketone and 2-hydroxy-1-(4-(2-hydroxyethoxy)-phenyl)-2-methylpropan-1-one.

Specific examples of the aminoacetophenone compound include α-aminoacetophenones such as 2-dimethylamino-2-methyl-1-phenylpropan-1-one, 2-diethylamino-2-methyl-1-phenylpropan-1-one, 2-methyl-2-morpholino-1-phenylpropan-1-one, 2-dimethylamino-2-methyl-1-(4-methylphenyl)propan-1-one, 2-dimethylamino-1-(4-ethylphenyl)-2-methylpropan-1-one, 2-dimethylamino-1-(4-isopropylphenyl)-2-methylpropan-1-one, 1-(4-butylphenyl)-2-dimethylamino-2-methylpropan-1-one, 2-dimethylamino-1-(4-methoxyphenyl)-2-methylpropan-1-one, 2-dimethylamino-2-methyl-1-(4-methylthiophenyl)propan-1-one, 2-methyl-1-[4-(methylthio)phenyl]-2-morpholino-propan-1-one, 2-benzyl-2-dimethylamino-1-(4-morpholinophenyl)-butan-1-one, and 2-benzyl-2-dimethylamino-1-(4-dimethylaminophenyl)butan-1-one.

Specific examples of another radical generator include benzoin methyl ether, benzoin ethyl ether, benzoin isopropyl ether, benzyl methyl ketal, α-halogenoacetophenones, methylphenylglyoxylate, benzyl, anthraquinone, phenanthrene quinone, acylphosphine oxide, α-acyloxime ester, benzyl and camphor quinone. The organic boron salt-based compound described in JP 2000-249822 A can be also used.

(2) Sensitizer

In the present invention, sensitizers commonly used in the general photopolymerization initiator systems can be used. Of those, one or more compounds selected from the group consisting of benzophenone-based compounds, thioxanthone-based compounds, and ketocoumarin-based compounds are preferably used as the sensitivity can rise more.

Specific examples of such a sensitizer include: a benzophenone-based compound such as benzophenone, 2,4,6-trimethylbenzophenone, 4-phenylbenzophenone, 4-benzoyl-4'-methyldiphenyl sulfide, 4,4'-bis(dimethylamino)benzophenone, or 4,4'-bis(diethylamino)benzophenone; a thioxanthone-based compound such as thioxanthone, 2-methylthioxanthone, 2,4-dimethylthioxanthone, 2,4-diethylthioxanthone, isopropylthioxanthone, 2,4-diisopropylthioxanthone or 2-chlorothioxanthone; and a ketocoumarin-based compound such as 3-acetylcoumarin, 3-acetyl-7-diethylaminocoumarin, 3-benzoylcoumarin, 3-benzoyl-7-diethylaminocoumarin, 3-benzoyl-7-methoxycoumarin, 3,3'-carbonylbiscoumarin, 3,3'-carbonylbis(7-methoxycoumarin) or 3,3'-carbonylbis(5,7-dimethoxycoumarin). Each of them may be used alone, or two or more kinds thereof may be used as a mixture.

The compounding ratio of each component in the photopolymerization initiator system (A) is as follows.

The content of the thiol compound having a fluorene skeleton represented by formula (1) is preferably 20 to 70% by mass, more preferably 30 to 60% by mass. If the content is less than 20% by mass, the photosensitivity and development latitude may decrease. On the other hand, if the content exceeds 70% by mass, the development property may deteriorate.

The content of the radical generator is preferably 20 to 80% by mass, more preferably 30 to 70% by mass. If the content is less than 20% by mass, the photosensitivity may decrease. On the other hand, if the content exceeds 80% by mass, the line width tends to be larger than the line width of photomask.

The content of the sensitizer is preferably 5 to 40% by mass, more preferably 10 to 30% by mass. If the content is less than 5% by mass, the photosensitivity may decrease. If the content exceeds 40% by mass, the light transmission toward the bottom of the photosensitive composition is prevented. Thus, a content in excess of 40% by mass is not preferable because of a decrease in resolution due to a change in cross sectional shape of the resist into an inverted-trapezoidal form.

2-2. Binder Resin having Carboxyl Group (B)

The binder resin (B) used in the present invention is one having a carboxyl group on its side chain, which is a component that predominantly determines the properties, such as the film strength, thermal resistance, substrate adhesiveness, solubility to an aqueous alkaline solution and alkaline development ability of resist.

Specific examples of the binder resin (B) include an acrylic copolymer (AP) having a carboxyl group, an epoxy (meth)acrylate resin (EA) having a carboxyl group and a urethane (meth)acrylate resin (UA) having a carboxyl group. From the viewpoint of adhesiveness with a glass substrate, the binder resin is preferably epoxy (meth)acrylate resin having a carboxyl group, more preferably bisphenol-type epoxy (meth)acrylate resin having a carboxyl group. Two or more of those binder resins having a carboxyl group may be used in combination.

(1) Acrylic Copolymer (AP) having Carboxyl Group

The acrylic copolymer having a carboxyl group can be obtained by copolymerizing:

(a) an ethylenically unsaturated monomer containing a carboxyl group; and (b) an ethylenically unsaturated monomer other than the above item (a).

The ethylenically unsaturated monomer (a) containing a carboxyl group is used for the purpose of providing the acrylic copolymer (AP) with alkaline development ability.

Specific examples of the ethylenically unsaturated monomer (a) containing a carboxyl group include (meth)acrylic acid, 2-(meth)acryloyloxyethyl succinate, 2-(meth)acryloyloxyethyl phthalate, (meth)acryloyloxyethyl hexahydrophthalate, (meth) acrylic acid dimer, maleic acid, crotonic acid, itaconic acid and fumaric acid.

The ethylenically unsaturated monomer (b) other than the above item (a) is used for the purpose of controlling the film strength and pigment dispersibility.

Specific examples of the ethylenically unsaturated monomer (b) other than the above item (a) include: a vinyl compound such as styrene, α-methylstyrene, (o,m,p-)hydroxystyrene, or vinyl acetate; (meth)acrylates such as methyl (meth)acrylate, ethyl (meth)acrylate, n-propyl (meth)acrylate, isopropyl (meth)acrylate, n-butyl (meth)acrylate, tert-butyl (meth)acrylate, n-hexyl (meth)acrylate, cyclohexyl (meth)acrylate, benzyl (meth)acrylate, phenoxyethyl (meth)acrylate, isobornyl (meth)acrylate, tetrahydrofurfuryl (meth)acrylate, (meth) acrylonitrile, glycidyl (meth)acrylate, allylglycidyl ether, 2-hydroxyethyl (meth)acrylate, 2-hydroxypropyl (meth)acrylate, N,N-dimethylaminoethyl (meth)acrylate, trifluoroethyl acrylate, 2,2,3,3-tetrafluoropropyl (meth)acrylate, or perfluorooctylethyl (meth)acrylate; a compound having an amide group such as (meth)acrylamide, N,N-dimethyl (meth)acrylamide, N,N-diethyl (meth) acrylamide, N-methyl (meth)acrylamide, N-ethyl (meth) acrylamide, N-isopropyl (meth)acrylamide, N-vinylpyrrolidone, N-vinylcaprolactam, or N-(meth) acryloyl morpholine.

An acrylic copolymer having an ethylenically unsaturated group on the side chain can be also used without any trouble, which is obtained by reacting an epoxy group of a compound having the epoxy group and an ethylenically unsaturated group in one molecule such as glycidyl (meth)acrylate, 3,4-epoxycyclohexyl methyl (meth)acrylate, 4-(2,3-epoxypropyl) butyl (meth)acrylate, or acrylglycidyl ether with a carboxyl group on the part of the side chain of an acrylic copolymer obtained by copolymerization of the above monomers, or by reacting part or whole of hydroxyl groups of an acrylic copolymer with an isocyanate group of a compound having the isocyanate group and an ethylenically unsaturated group in one molecule such as 2-methacryloyloxyethyl isocyanate.

The copolymerization ratio between the ethylenically unsaturated monomer (a) containing a carboxyl group and the ethylenically unsaturated monomer (b) other than the above item (a) is preferably 5:95 to 40:60, more preferably 10:90 to 50:50. If the copolymerization ratio of the above item (a) is less than 5, the pattern formation may become difficult because of a decrease in alkaline development ability. In addition, if the copolymerization ratio of the above item (a) exceeds 60, the line width may be hardly kept constant because the alkaline development of a photo-cured portion tends to proceed.

The molecular weight of the acrylic copolymer having a carboxyl group and an ethylenically unsaturated group is preferably in the range of 1,000 to 500,000, more preferably 3,000 to 200,000 in terms of polystyrene-equivalent mass average molecular weight with GPC. If the molecular weight is less than 1,000, the film strength may decrease extremely. On the other hand, if the molecular weight exceeds 500,000, the alkaline development ability may decrease extremely.

(2) Epoxy (Meth)Acrylate Resin (EA) having Carboxyl Group

A suitable epoxy (meth)acrylate resin (EA) having a carboxyl group to be used in the present invention is, but not specifically limited to, an epoxy (meth)acrylate compound obtained by reacting an acid anhydride with a product of the reaction between an epoxy resin or an epoxy compound and an unsaturated group-containing monocarboxylic acid.

Examples of the epoxy resin to be reacted with an unsaturated group-containing monocarboxylic acid include a bisphenol A type epoxy resin, a hydrogenated bisphenol A type epoxy resin, a brominated bisphenol A type epoxy resin, a bisphenol F type epoxy resin, a bisphenol S type epoxy resin, a novolac type epoxy resin, a phenol novolac type epoxy resin, a cresol novolac type epoxy resin, a triphenylmethane type epoxy resin, a naphthalene type epoxy resin, an N-glycidyl type epoxy resin, a dicyclopentadiene phenolic epoxy resin, a diglycidylphthalate resin, a heterocyclic epoxy resin, a bixylenol type epoxy resin and a biphenyl type epoxy resin. Each of them is used alone, or two or more kinds thereof are used in combination.

Examples of the epoxy compound to be reacted with the unsaturated group-containing monocarboxylic acid include, but are not particularly limited to, epoxy compounds such as a bisphenol A type epoxy compound, a bisphenol F type epoxy compound, a bisphenol S type epoxy compound, a phenolnovolac type epoxy compound, a cresolnovolac type epoxy compound and an aliphatic epoxy compound. Each of them can be used alone, or two or more kinds thereof can be used in combination.

Examples of the unsaturated group-containing monocarboxylic acid to be reacted with the epoxy resin or epoxy compound include (meth)acrylic acid, 2-(meth)acryloyloxyethyl succinate, 2-(meth)acryloyloxyethyl phthalate, (meth) acryloyloxyethyl hexahydrophthalate, (meth) acrylic dimer, β-furfuryl acrylic acid, β-styryl acrylic acid, cinnamic acid, crotonic acid and α-cyano cinnamic acid. Examples of such unsaturated group-containing monocarboxylic acid further include a half ester compound as a reaction product of a hydroxyl group-containing acrylate and a saturated or unsaturated dibasic anhydride, and a half ester compound as a reaction product of an unsaturated group-containing monoglycidyl ether and a saturated or unsaturated dibasic anhydride. Each of the unsaturated group-containing monocarboxylic acids can be used alone or two or more kinds thereof can be used in combination.

Examples of the acid anhydride include: a dibasic anhydride such as maleic anhydride, succinic anhydride, itaconic anhydride, phthalic anhydride, tetrahydrophthalic anhydride, hexahydrophthalic anhydride, methylhexahydrophthalic anhydride, endomethylenetetrahydrophthalic anhydride, methylendomethylenetetrahydrophthalic anhydride, chlorendic anhydride, or methyltetrahydrophthalic anhydride; an aromatic polycarboxylic anhydride such as trimellitic anhydride, pyromellitic anhydride, or benzophenonetetracarboxylic dianhydride; and a polycarboxylic anhydride derivative such as 5-(2,5-dioxotetrahydrofurfuryl)-3-methyl-3-cyclohexene-1,2-dicalboxylic anhydride or endobicyclo-[2,2,1]-hept-5-ene-2,3-dicalboxylic anhydride. Each of them can be used alone or two or more kinds thereof can be used in combination.

The epoxy (meth)acrylate resin (EA) having a carboxyl group thus obtained has, but not specifically limited to, a molecular weight of preferably 1,000 to 40,000, more preferably 2,000 to 5,000 in terms of a polystyrene-equivalent mass average molecular weight with GPC.

In addition, the acid value of the epoxy (meth)acrylate resin (EA) (means a solid acid value measured in accordance with JIS K0070, the same will be applied in the following description) is preferably 10 mgKOH/g or more, more preferably in the range of 45 to 160 mgKOH/g, further preferably in the range of 50 to 140 mgKOH/g because of a good balance between the alkali solubility and the alkaline resistance of a cured film. If the acid value is less than 10 mgKOH/g, the alkaline solubility may decrease. On the other hand, an excessively large acid value may become a factor that lowers the characteristic features of the cured film, such as alkaline resistance of a cured film, depending on the combination of constituent components of the photosensitive composition.

(3) Urethane (Meth)Acrylate Resin (UA) having Carboxyl Group

The urethane (meth)acrylate resin (UA) having a carboxyl group used in the present invention is a binder resin which is more flexible than the acrylic copolymer (AP) or the epoxy (meth)acrylate resin (EA), so that it will be used in the applications that require flexibility and flexing resistance.

The urethane (meth)acrylate resin (UA) having a carboxyl group contains a unit originated from (meth)acrylate having a hydroxyl group, a unit originated from polyol and a unit originated from polyisocyanate. More specifically, it is constructed of a unit originated from (meth)acrylate having hydroxyl groups on its both ends. A structure between those both ends is constructed of a repetitive unit consisting of a unit originated from polyol and a unit originated from polyisocyanate which are coupled by a urethane bond and a carboxyl group is present in the repetitive unit.

That is, the repetitive structure of the urethane (meth)acrylate resin (UA) having a carboxyl group can be represented by formula (20).

  (20)

In formula (20), ORbO represents a dehydrogenation residue of polyol and Rc represents a deisocyanate residue of polyisocyanate.

The urethane (meth)acrylate resin (UA) having a carboxyl group can be produced by carrying out a reaction of at least (meth)acrylate having a hydroxyl group and polyol and/or polyisocyanate. Here, at least either of the polyol and the polyisocyanate should be a compound having a carboxyl group. Preferably, polyol having a carboxyl group is used. In this way, by the use of the compound having a carboxyl group as polyol and/or polyisocyanate, the urethane (meth)acrylate resin (UA) in which a carboxyl group is present in Rb or Rc can be produced.

Here, in the above formula (20), the integer n is preferably about 1 to 200, more preferably 2 to 30. If n is within such ranges, the flexibility of the cured film may be more excellent.

Furthermore, if two or more kinds of at least one of polyol and polyisocyanate are used, the repetitive unit may represent plural kinds. The regularity of the plural units can be suitably selected from complete random, block, localization and the like depending on a purpose.

Examples of the (meth)acrylate having a hydroxyl group include 2-hydroxyethyl (meth)acrylate, hydroxypropyl (meth)acrylate, hydroxybutyl (meth)acrylate, a caprolactone or alkylene oxide adduct of each of the above-described (meth)acrylate, glycerin mono(meth)acrylate, glycerin di(meth)acrylate, a glycidyl methacrylate-acrylic acid adduct, trimethylolpropane mono(meth)acrylate, trimethylol di(meth)acrylate, pentaerythritol tri(meth)acrylate, dipentaerythritol penta(meth)acrylate and a trimethylolpropane-alkylene oxide adduct-di(meth)acrylate. The (meth)acrylate (a) having a hydroxyl group can be used alone or two or more kinds thereof can be used in combination. Of those, 2-hydroxyethyl (meth)acrylate, hydroxypropyl (meth)acrylate, and hydroxybutyl (meth)acrylate are preferable, and 2-hydroxyethyl (meth)acrylate is more preferable. The use of 2-hydroxyethyl (meth)acrylate further facilitates the synthesis of a urethane (meth)acrylate (UA) resin containing a carboxyl group.

A polymer polyol and/or dihydroxyl compound can be used as polyol to be used in the present invention. Examples of the polymer polyol include: a polyether-based diol such as polyethylene glycol, polypropylene glycol, or polytetramethylene glycol; a polyester-based polyol obtained by a reaction between polyhydric alcohol and ester of polybasic acid; a polycarbonate-based diol having a unit derived from such as hexamethylene carbonate or pentamethylene carbonate as a constitutional unit; and a polylactone-based diol such as polycaprolactone diol or polybutyrolactone diol.

Furthermore, when polymer polyol having a carboxyl group is used as the above polyol having a carboxyl group, for example, it is also capable of using a polymer polyol synthesized such that a carboxyl group remains by means of the co-existence of a polybasic acid of trivalent or more, such as (anhydrous) trimellitic acid, at the time of synthesis.

One kind of polymer polyol may be used, or two or more kinds of polymer polyol may be used in combination. In addition, for those polymer polyols, those each having an average molecular weight of 200 to 2,000 are preferably used because the cured film becomes more excellent in flexibility.

A branched- or linear-chain compound having two alcoholic hydroxyl groups can be used as the above dihydroxyl compound. However, it is particularly preferable to use a dihydroxy aliphatic carboxylic acid having a carboxyl group. Such a dihydroxyl compound may be dimethylol propionic acid or dimethylol butanoic acid. The use of the dihydroxy aliphatic carboxylic acid having a carboxyl group can facilitate the presence of a carboxyl group in a urethane (meth)acrylate resin (UA). Each of those dihydroxyl compounds may be used singly or two or more of them may be used in combination. In addition, the dihydroxyl compound may be used together with polymer polyol.

In addition, in the case of using the polymer polyol having a carboxyl group in combination, or using polyisocyanate having a carboxyl group as the polyisocyanate described below, a dihydroxyl compound having no carboxyl group (for example, ethylene glycol, diethylene glycol, propylene glycol, 1,4-butanediol, 1,3-butanediol, 1,5-pentanediol, neopentyl glycol, 3-methyl-1,5-pentanediol, 1,6-hexanediol, or 1,4-cyclohexanedimethanol) may be used as the hydroxyl compound.

Specific examples of polyisocyanate to be used in the present invention include diisocyanates such as 2,4-toluene diisocyanate, 2,6-toluene diisocyanate, isophorone diisocyanate, hexamethylene diisocyanate, diphenylmethylene diisocyanate, (o, m, or p)-xylene diisocyanate, methylene bis(cyclohexyl isocyanate), trimethylhexamethylene diisocyanate, cyclohexane-1,3-dimethylene diisocyanate, cyclohexane-1,4-dimethylene diisocyanate, and 1,5-naphthalene diisocyanate. The polyisocyanate can be used alone or two or more kinds thereof can be in combination. A polyisocyanate having a carboxyl group can also be used.

The urethane (meth)acrylate resin (UA) having a carboxyl group used in the present invention has, but not specifically limited to, a molecular weight of 1,000 to 40,000, preferably 8,000 to 30,000 in terms of polystyrene-equivalent mass average molecular weight with GPC. If the mass average molecular weight of the urethane (meth)acrylate resin (UA) having a carboxyl group is less than 1,000, the elasticity and strength of the cured film may deteriorate. On the other hand, a mass average molecular weight of more than 40,000 may lower the flexibility of the film because the resin is cured. Furthermore, the acid value of the urethane (meth)acrylate resin (UA) is preferably 5 to 150 mgKOH/g, more preferably 30 to 120 mgKOH/g. If the acid value is less than 5 mgKOH/g, the alkaline solubility of the resist curable resin composition may decrease. On the other hand, if the acid value exceeds 150 mgKOH/g, the alkaline resistance or the like of the cured film may deteriorate.

2-3. Compound (C) having Ethylenically Unsaturated Group

The compound (C) having an ethylenically unsaturated group, which is contained in the photosensitive composition of the present invention, is other than the binder resin (B) described above and may be used for the purpose of adjusting the photosensitivity of the photosensitive composition or adjusting the physical properties of a cured product made of the photosensitive composition, such as thermal resistance and flexibility. Preferably, (meth)acrylate ester is used.

Specific examples of the compound (C) having an ethylenically unsaturated group include: alkyl (meth)acrylate (such as methyl (meth)acrylate, ethyl (meth)acrylate, propyl (meth)acrylate, n-butyl (meth)acrylate, isobutyl (meth)acrylate, sec-butyl (meth)acrylate, tert-butyl (meth)acrylate, hexyl (meth)acrylate, octyl (meth)acrylate, isooctyl (meth)

acrylate, 2-ethylhexyl (meth)acrylate, decyl (meth)acrylate, lauryl (meth)acrylate, or stearyl (meth)acrylate);

alicyclic (meth)acrylate (such as cyclohexyl (meth)acrylate, bornyl (meth)acrylate, isobornyl (meth)acrylate, dicyclopentenyl (meth)acrylate, or dicyclopentenyloxyethyl (meth)acrylate); aromatic (meth)acrylate (such as benzyl (meth)acrylate, phenyl (meth)acrylate, phenylcarbitol (meth)acrylate, nonylphenyl (meth)acrylate, nonylphenylcarbitol (meth)acrylate, or nonylphenoxy (meth)acrylate);

(meth)acrylate having a hydroxyl group (such as 2-hydroxyethyl (meth)acrylate, hydroxypropyl (meth)acrylate, hydroxybutyl (meth)acrylate, butanediol mono(meth)acrylate, glycerol (meth)acrylate, polyethylene glycol (meth)acrylate, or glycerol di(meth)acrylate);

(meth)acrylate having an amino group (such as 2-dimethylaminoethyl (meth)acrylate, 2-diethylaminoethyl (meth)acrylate, or 2-tert-butylaminoethyl (meth)acrylate);

methacrylate having a phosphorus atom (such as methacryloxyethyl phosphate, bis-methacryloxyethyl phosphate, or methacryloxyethyl phenyl acid phosphate);

di(meth)acrylate (such as ethylene glycol di(meth)acrylate, diethylene glycol di(meth)acrylate, triethylene glycol di(meth)acrylate, tetraethylene di(meth)acrylate, polyethylene glycol di(meth)acrylate, propylene glycol di(meth)acrylate, dipropylene glycol di(meth)acrylate, tripropylene glycol di(meth)acrylate, 1,4-butanediol di(meth)acrylate, 1,3-butanediol di(meth)acrylate, neopentyl glycol di(meth)acrylate, 1,6-hexanediol di(meth)acrylate, bis-glycidyl (meth)acrylate) or dimethylol tricyclodecane di(meth)acrylate;

poly(meth)acrylate (such as trimethylolpropane tri(meth)acrylate, pentaerythritol tri(meth)acrylate, or dipentaerythritol hexa (meth)acrylate);

modified polyol poly(meth)acrylate (such as a di(meth)acrylate of 4-mol ethylene oxide adduct of bisphenol S, a di(meth)acrylate of 4-mol ethylene oxide adduct of bisphenol A, aliphatic-modified pentaerythritol di(meth)acrylate, a tri(meth)acrylate of 3-mol propylene oxide adduct of trimethylolpropane, or a tri(meth)acrylate of 6-mol propylene oxide adduct of trimethylolpropane);

polyacrylate having an isocyanuric acid skeleton (such as bis(acryloyloxyethyl) monohydroxyethyl isocyanurate, tris(acryloyloxyethyl) isocyanurate, or tris(acryloyloxyethyl) isocyanurate of $\epsilon$-caprolactone adduct);

polyester acrylate (such as $\alpha,\omega$-diacryloyl-(bisethyleneglycol) phthalate or $\alpha,\omega$-tetraacryloyl-(bistrimethylolpropane)-tetrahydrophthalate);

glycidyl (meth)acrylate;

allyl (meth)acrylate;

$\omega$-hydroxyhexanoyloxyethyl (meth)acrylate;

polycaprolactone (meth)acrylate;

(meth)acryloyloxyethyl phthalate;

(meth)acryloyloxyethyl succinate;

2-hydroxy-3-phenoxypropylacrylate; and phenoxyethyl acrylate.

In addition, an N-vinyl compound (such as N-vinylpyrrolidone, N-vinylformamide, or N-vinylacetamide), polyester (meth)acrylate, urethane (meth)acrylate, epoxy (meth)acrylate or the like can be suitably used as a compound having an ethylenically unsaturated group.

Of those, preferable examples include poly(meth)acrylate such as: a di(meth)acrylate of 4-mol ethyleneoxide adduct of bisphenol A, a di(meth)acrylate of 4-mol propyleneoxide adduct of bisphenol A or dimethylol tricyclodecane di(meth)acrylate in terms of a pattern configuration; and trimethylolpropane tri(meth)acrylate, pentaerythrytol tetra(meth)acrylate or dipentaerythrytol hexa(meth)acrylate in terms of photosensitivity.

2-4. Pigment (D)

The photosensitive composition of the present invention may be added with the pigments (D) listed below (represented by color index numbers, respectively):

Examples of the pigment include: C.I. Pigment Yellow 12, 13, 14, 17, 20, 24, 55, 83, 86, 93, 109, 110, 117, 125, 137, 139, 147, 148, 153, 154, 166, or 168; C.I. Pigment Orange 36, 43, 51, 55, 59, or 61; C.I. Pigment Red 9, 97, 122, 123, 149, 168, 177, 180, 192, 215, 216, 217, 220, 223, 224, 226, 227, 228, or 240; C.I. Pigment Violet 19, 23, 29, 30, 37, 40, or 50; C.I. Pigment Blue 15, 15:1, 15:4, 15:6, 22, 60, or 64; C.I. Pigment Green 7 or 36; C.I. Pigment Brown 23, 25, or 26; C.I. Pigment Black 7; and titanium black. Each of the pigments may be used alone, or two or more of them may be used in combination.

As a black pigment (D) to be used for the black matrix resist composition of the present invention, carbon black, acetylene black, lampblack, graphite, iron black, aniline black, cyanine black, titanium black or three-color (red, green, blue) organic pigments by mixture can be used as a black pigment.

Among these, carbon black and titanium black are specifically preferable in view of light blocking ratio and characteristics of a printed image. Examples of the carbon black include the following carbon blacks commercially available:

Products of Mitsubishi Chemical Corporation: MA7, MA8, MA11, MA100, MA220, MA230, #52, #50, #47, #45, #2700, #2650, #2200, #1000, #990, #900.

Products of Degussa Japan Co., Ltd.: Printex95, Printex90, Printex85, Printex75, Printex55, Printex45, Printex40, Printex30, Printex3, PrintexA, PrintexG, SpecialBlack4, SpecialBlack550, SpecialBlack350, SpecialBlack250, SpecialBlack100.

Products of Cabot Corporation: Monarch460, Monarch430, Monarch280, Monarch120, Monarch800, Monarch4630, REGAL99, REGAL99R, REGAL415, REGAL415R, REGAL250, REGAL250R, REGAL330, BLACK PEARLS480, PEARLS130.

Products of Columbian Chemicals Company: Raven11, Raven15, Raven30, Raven35, Raven40, Raven410, Raven420, Raven450, Raven500, Raven780, Raven850, Raven890H, Raven1000, Raven1020, Raven1040, Raven1060, Raven1080, Raven1255.

Examples of the titanium black include 13M-C, produced by Mitsubishi Materials Corporation.

The above-mentioned black pigments may be used in combination. In particular, using carbon black and titanium black in combination can enhance the light blocking effect of the black matrix resist composition compared with the case where each of them is used alone.

2-5. Solvent (E)

Further, according to use of the product, various additives may be added to the photosensitive composition of the present invention in order to impart viscosity, operability, characteristics of the cured product, and the like. For example, solvents (E) may be added for the purposes of sufficient dispersibility of each component, improvement of operability and adhesion at the time of coating, or adjustment of viscosity.

Specific examples of the volatile solvent (E) to be used for the photosensitive composition of the present invention include alcohols, ketones and esters. Examples of such volatile solvent include methanol, ethanol, toluene, xylene, ethylbenzene, cyclohexane, isophorone, cellosolve acetate, diethylene glycol dimethyl ether, ethylene glycol diethyl ether, ethylene glycol monoethyl ether, ethylene glycol monobutyl ether, propylene glycol monomethyl ether, propylene glycol monomethyl ether acetate, propylene glycol monoethyl ether acetate, diethylene glycol monoethyl ether acetate, isoamyl acetate, ethyl lactate, γ-butyrolactone, methylethyl ketone, acetone, and cyclohexanone. Each of them can be used alone, or two or more kinds thereof can be used as a mixture.

Further, when it is difficult to use the above-described volatile solvent depending on purposes, a reactive solvent (E) can be used. Specific examples of such reactive solvent include 2-hydroxyethyl(meth)acrylate, methyl (meth)acrylate, n-butyl (meth)acrylate, cyclohexyl (meth)acrylate, isobornyl (meth)acrylate, N,N-dimethylaminoethyl (meth)acrylate, N-acryloylmorpholine, N-acryloylpiperidine, N,N-dimethyl (meth)acrylamide, N-vinylpyrrolidone and N-vinylacetamide. Each of them can be used alone, or two or more kinds thereof can be used as a mixture. The above-described volatile solvent may be further added to the reactive solvent as required.

The organic solvent (E) to be used for the black matrix resist composition of the present invention is not particularly limited as long as the organic solvent can dissolve and disperse each of the above-described components constituting the black matrix resist composition of the present invention. Specific examples thereof include methanol, ethanol, isopropanol, toluene, xylene, ethylbenzene, cyclohexane, isophorone, cellosolve acetate, diethyleneglycol dimethyl ether, ethyleneglycol diethyl ether, methyl cellosolve, ethyl cellosolve, butyl cellosolve, propyleneglycol monomethyl ether, propyleneglycol monomethyl ether acetate, propyleneglycol monoethyl ether acetate, diethyleneglycol ethyl ether acetate, methyl methoxypropionate, ethyl methoxypropionate, methyl ethoxypropionate, ethyl ethoxypropionate, ethyl acetate, isoamyl acetate, ethyl lactate, acetone, methyl ethyl ketone, cyclohexanone, N,N-dimethylformamide and N-methylpyrrolidone. Each of them is used alone, or two or more kinds thereof are used in combination.

It is desirable to prepare the black matrix resist composition of the present invention so as to be of a solid concentration of 5 to 30% by mass, preferably 10 to 25% by mass, using any of those organic solvents.

2-6. Other Optional Components

The black matrix resist composition of the present invention may be suitably added with, in addition to the above essential components, a pigment dispersant, an adhesion-improving agent, a leveling agent, a development improver, an oxidation inhibitor, a thermal polymerization inhibitor or the like. In particular, in the coloring composition, a pigment dispersant is desirably mixed in certain instances because it is important for quality stability to finely disperse a coloring material and to stabilize the state of being dispersed.

The pigment dispersant has an affinity to both of the pigment and the binder resin, and examples thereof include nonionic, cationic and anionic surfactants and polymer dispersants. Of those, polymer dispersants are preferable. In particular, a polymer dispersant containing: a basic functional group, for example a nitrogen-containing heterocyclic group such as a primary, secondary or tertiary amino group, pyridine, pyrimidine or pyrazine; or a functional group such as an amide group or a urethane group, may be advantageously used.

The photosensitive composition and black matrix resist composition of the present invention may further contain fluorescent whiteners, surfactants, plasticizers, flame-retardants, antioxidants, UV absorbents, foaming agents, fungicides, antistatic agents, magnetic materials, electrically conductive materials, antimicrobial/bactericidal materials, porous adsorbents, perfumes and the like, depending on the purpose.

Also, the photosensitive composition and black matrix resist composition of the present invention may contain a heat polymerization inhibitor in order to prevent polymerization during storage. Specific examples of the heat polymerization inhibitor include p-methoxyphenol, hydroquinone, catechol, tert-butylcatechol, phenothiazine and methoquinone.

2-7. Compounding Ratio of Photosensitive Composition

The compounding ratio of the photopolymerization initiator system (A) in the photosensitive composition of the present invention is preferably 1 to 40% by mass, more preferably 3 to 30% by mass. If the ratio is less than 1% by mass, the photosensitivity may deteriorate. If the ratio exceeds 40% by mass, the mechanical strength of the cured product may decrease.

The compounding ratio between the binder resin (B) and the compound (C) having an ethylenically unsaturated group ((B):(C)) is 95:5 to 50:50, preferably 90:10 to 60:40, more preferably 85:15 to 70:30 in mass ratio. If the compounding ratio of the binder resin (B) exceeds 95 or more, the photosensitivity may deteriorate. On the other hand, a compounding ratio of the binder resin (B) of less than 50 is not preferable because the line width of patterns tends to thicken.

2-8. Compounding Ratio of Black Matrix Resist Composition

A compounding ratio of each of the components in the black matrix resist composition of the present invention is not particularly limited but the ratio of each component except the organic solvent (E) to the total content (total solid content) is preferably defined within the following ranges.

(A) The content of the photopolymerization initiator system is preferably 2 to 15% by mass, more preferably 5 to 10% by mass. If the content of the photopolymerization initiator system is too small, the photosensitivity and development latitude may decrease. If the content is too large, the width of the resist pattern tends to be larger than the line width of a photomask.

(B) The content of the binder resin having a carboxyl group is preferably 10 to 30% by mass, more preferably 15 to 25% by mass. If the content of the binder resin is too small, adhesiveness of the binder with a substrate may decrease or development latitude may decrease. If the content is too large, light-blocking effect may decrease.

(C) The content of the compound having an ethylenically unsaturated group is preferably 20% by mass, more preferably 3 to 15% by mass. If the content of the compound having an ethylenically unsaturated group is too small, the photosensitivity may decrease. If the content is too large, the width of the resist patterns tends to be larger than the line width of a photomask.

(D) The content of the black pigment is preferably 40 to 80% by mass, more preferably 45 to 70% by mass. If the content of the black pigment is too small, the light-blocking effect may decrease. If the content is too large, the photosensitivity and adhesiveness with the substrate may decrease.

3. Production Method and Use of Photosensitive Composition

The photosensitive composition containing a pigment can be produced by using various kinds of dispersing means such as a three-roll mill, a two-roll mill, a sand mill, an attritor, a ball mill, a kneader and a paint shaker. To prevent the occurrence of gelling by polymerization reaction or the like at the time of dispersing, a polymerization inhibitor may be added. The monomer and photopolymerization initiator may be compounded after the pigment is dispersed. In addition, to disperse pigments well, a dispersing agent may be added as appropriate. The dispersing agent helps pigments to be dispersed and prevents reagglomeration after the dispersion. For the purpose of obtaining appropriate flowability or obtaining the light-shielding property, and mechanical and physical characteristics of the cured product, an extender pigment such as barium sulfate, calcium carbonate, silica, titania, alumina or aluminum powder may be added to the photosensitive composition of the present invention.

The photosensitive composition of the present invention may be applied to a substrate such as glass, aluminum, a PET film or a polyester film by a coating method such as spray coating, spinner coating, roll coating, screen coating, spread coating, dip coating or calendar coating. Here, in order to obtain appropriate coating characteristics, a small amount of silicone- or fluorine-based surfactant as a leveling agent or defoaming agent may be added to the photosensitive composition of the present invention.

The photosensitive composition coated by means of any one of the above coating methods is dried as required by a hot-air oven or a hot plate generally under conditions of 60 to 100° C. for 10 to 30 minutes to evaporate the volatile solvent. If the drying temperature is too high or the heating time is too long, polymerization or cross-linking partially occurs, so that the solubility of an unexposed portion in the developer is decreased leading to so-called burn, which is undesirable. Drying may be performed under reduced pressure.

The methods of forming a pattern of a certain configuration with the photosensitive composition of the present invention are roughly classified into two types. One is a method comprising coating the photosensitive composition in a desired configuration and then curing it by irradiation with light. The other is a method comprising applying the photosensitive composition evenly onto a substrate, irradiating the photosensitive composition with light to cure the photosensitive composition so that the exposed portion forms a desired configuration, and then removing an unexposed portion by using means such as washing, peeling, physical polishing, chemical polishing or the like to form a pattern with the remaining photo-cured product. In the case of the photosensitive composition of the present invention, in particular, a suitable pattern can be formed by the latter method of pattern formation.

Inorganic materials such as glass and silicon; metallic materials such as aluminum, stainless steel and copper; resin materials such as PET, polyester, polyimide, epoxy resin, polyethylene and polycarbonate; and paper and the like may be used for the substrate used in the pattern formation of the present invention. The surface of the substrate may be subjected to oxidation treatment, acid treatment, plasma treatment, discharge treatment or the like to improve adhesion of the photosensitive composition. Since the photosensitive composition is usually present on the surface of a substrate, the thickness of the substrate can be set optionally. A resin layer or the like that does not participate in the photoreaction may be provided between the photosensitive composition and the substrate.

In the above-described pattern formation, when an uncured portion of the photosensitive composition after light irradiation is dissolved and removed to be subjected to development treatment, examples of a solvent for a developer include N-methylpyrrolidone, methanol, ethanol, toluene, cyclohexane, isophorone, cellosolve acetate, diethylene glycol dimethyl ether, ethylene glycol diethyl ether, xylene, ethylbenzene, methyl cellosolve, ethyl cellosolve, butyl cellosolve, propylene glycol monomethyl ether, propylene glycol monomethyl ether acetate, isoamyl acetate, ethyl lactate, methylethyl ketone, acetone, cyclohexanone, N,N-dimethyl formamide, acetonitrile and an alkali aqueous solution. Each of them may be used alone, or two or more kinds thereof can be used in combination. A basic substance such as trimethylamine or triethylamine or a surfactant may be further added to the solvent.

Examples of the alkali aqueous solution include an aqueous solution of an inorganic salt such as sodium hydroxide, potassium hydroxide, sodium carbonate or potassium carbonate; and an aqueous solution of an organic salt such as hydroxytetramethyl ammonium or hydroxytetraethyl ammonium. Each of them may be used alone, or two or more kinds thereof can be used in combination.

The photosensitive composition of the present invention can be suitably used particularly for a development type resist that forms fine patterns. Specific examples thereof include optical plate making resists, solder resists, etching resists, color filter resists, holograms, optical sculpturing and UV ink.

4. Production Method of Black Matrix Resist Composition

The black matrix resist composition of the present invention can be produced by: mixing or premixing (B) a binder resin having a carboxyl group, (E) an organic solvent, (D) a black pigment, and optionally a pigment dispersant; subjecting the mixture to a dispersing treatment, and further mixing and dissolving (C) a compound having an ethylenically unsaturated group and (A) a photopolymerization initiator system into the resultant.

A disperser for carrying out the dispersion treatment may be any one of roll mills such as a two-roll mill and a three-roll mill; ball mills such as a ball mill and a vibration ball mill; a paint conditioner; beads mills such as a continuous disk type beads mill, and a continuous annular type beads mill. Of those, in particular, the continuous annular type beads mill is preferable because it is capable of carrying out pulverization and dispersion within a short time, it attains a sharp distribution of particle diameters after dispersion, and it allows an easy temperature controls during pulverization and dispersion to prevent a dispersion liquid from deterioration.

The continuous annular type beads mill has a structure wherein a rotor (body of rotation) having grooves thereon for stirring beads is inserted into a vessel (cylindrical body) having an inlet and an outlet for the material. The beads are moved by the rotation of the rotor in the gap portion of the double cylinders made up of the vessel and the rotor to carry out pulverization, shearing and grinding to effectively pulverize and disperse the black pigment. The sample is introduced through the end portion of the vessel and then formed into fine particles, followed by being discharged from the opposite side of the inlet. This treatment is repeated until the desired particle size distribution is obtained. The term "retaining period" refers to a time period in which the sample is actually pulverized and dispersed in the vessel.

Such a continuous annular type beads mill may be, for example, SPIKE MILL (trade name) manufactured by Inoue Manufacturing, Inc., or OB-MILL (trade name) manufactured by Turbo Kogyo Co., Ltd.

Preferable dispersion conditions for a continuous annular type beads mill are as follows. The bead size (diameter) used is preferably 0.2 to 1.5 mm, more preferably 0.4 to 1.0 mm. If the bead size is less than 0.2 mm, the weight of a single bead is too small, which reduces the pulverization energy of the single bead and retards the pulverization of the pigment. If the bead size exceeds 1.5 mm, the collision frequency between the beads decreases and it becomes difficult to carry out the pulverization of carbon black within a short time. For the materials of beads, those having a specific gravity of 4 or more including ceramics such as zirconia and alumina and stainless steel are preferable because they improves pulverization efficiency.

The peripheral speed of the rotor is preferably 5 to 20 m/second, more preferably 8 to 15 m/second. If the peripheral speed is less than 5 m/second, the pigment cannot be pulverized and dispersed sufficiently. The peripheral speed exceeding 20 m/second is unfavorable since the temperature of the pigment dispersion rises excessively due to frictional heat and degeneration such as thickening may occur.

Temperatures at dispersion are within the range of 10 to 60° C., more preferably within the range of room temperature to 50° C. A temperature of lower than 10° C. is not preferable because the dispersion solution may be mixed with atmospheric moisture owing to dew condensation. A temperature in excess of 60° C. is not preferable because degeneration such as thickening may occur.

The retaining period is preferably 1 to 30 minutes, more preferably 3 to 20 minutes. If the retaining period is shorter than one minute, the pulverization and dispersion treatments may be insufficient. If the retaining period exceeds 30 minutes, the dispersion solution may be deteriorated and then thickened.

5. Manufacturing Method of Color Filter

A method of manufacturing a color filter using the black matrix resist compound of the present invention will be described. Here, the description will be made with reference to a color filter for a liquid crystal display device, where a black matrix resist composition, pixels and a protective film are laminated in this order.

The black matrix resist composition of the present invention is applied on a transparent substrate. Then, after a solvent has been dried in an oven or the like, black matrix patterns are formed by exposure development through a photomask and subjected to post baking, thereby completing the formation of a black matrix.

Examples of the transparent substrate include, but not particularly limited to: inorganic glass such as quartz glass, borosilicate glass, and lime soda glass having a silica-coated surface; and films and sheets of thermoplastics including polyesters such as polyethylene terephthalate, polyolefins such as polypropylene and polyethylene, polycarbonate, polymethylmethacrylate and polysulfone; and those of thermosetting plastics such as epoxy resin and a polyester resin. Those transparent substrates may be previously subjected to any one of a corona discharge treatment, an ozone treatment, or a thin film treatment with various polymers such as a silane-coupling agent and a urethane polymer in order to improve physical properties such as adhesiveness of the substrate surface.

For the coating methods, dip coating; those using a role coater, a wire bar, a flow coater and a die coater; spray coating, and a rotary method using a spinner or the like may be suitably used.

A solvent is dried by a drying device such as a hot plate, an IR oven or a convection oven. Preferable drying conditions include a temperature of 40 to 150° C. and a drying time period within 10 seconds to 60 minutes. Alternatively, the solvent may be dried in a vacuum.

An exposure method comprises: providing a 50-200 µm space (gap) on the sample; placing a photomask thereon; and carrying out an image exposure. Examples of light source which can be used for exposure include: lamp light source such as a xenon lamp, a high pressure mercury lamp, an ultra-high pressure mercury lamp, a metal halide lamp, a moderate pressure mercury lamp, and a low-pressure mercury lamp; and laser source such as an argon ion laser, a YAG laser, an excimer laser and a nitrogen laser. When only light having a specific irradiation wavelength is used, an optical filter may be used.

The developing process is carried out using a liquid developer to develop a resist by a dipping, shower or paddle method or the like. The liquid developer is not particularly limited as far as it is a solvent capable of dissolving a resist film on an unexposed portion. For instance, organic solvents including acetone, methylene chloride, trichlene and cyclohexanone can be used, but many of the organic solvents may cause environmental pollution, hazardousness to the human body and fire hazard. Therefore, it is preferable to use an alkali liquid developer having no such risks. Examples of the alkali liquid developer include aqueous solutions containing: inorganic alkali agents such as sodium carbonate, potassium carbonate, sodium silicate, potassium silicate, sodium hydroxide and potassium hydroxide; and organic alkali agents such as diethanolamine, triethanolamine and tetra alkyl ammonium hydroxide. If required, a surfactant, a water-soluble organic solvent, and a low molecular compound having a hydroxyl group or a carboxyl group may be added to the alkali liquid developer. In particular, it is preferable to add a surfactant because it has improving effects on the development property, resolution, scumming or the like.

The surfactants for the liquid developer include: anionic surfactants each having a sodium naphthalenesulfonate group or a sodium benzenesulfonate group; nonionic surfactants each having a polyalkyleneoxy group; and cationic surfactants each having a tetraalkylammonium group. A method of development is not particularly limited but in general the development is carried out at a development temperature of preferably 10 to 50° C., more preferably 15 to 45° C. by means of a method such as immersion development, spray development, brush development, or supersonic wave development.

Post baking is performed at temperatures ranging from 150 to 300° C. for a time period of 1 to 120 minutes using the same apparatus as one used in drying the solvent.

The black matrix thus obtained has a film thickness preferably in the range of 0.1 to 1.5 µm, more preferably in the range of 0.2 to 1.2 µm. Furthermore, the optical density of the black matrix having the film thickness in the above range is preferably 3 or more for attaining the functions.

This step forms black matrix patterns with an opening of about 20 to 200 µm between the black matrices. In the post process, pixels will be formed in this space.

Next, pixels of plural colors are formed in the opening of the black matrix. The colors of the respective pixels is usually any of three colors of red (R), green (G) and blue (B), and a photosensitive composition is thus stained with a pigment or dye. At first, the colored photosensitive composition is applied on a transparent substrate on which black matrix patterns are placed. Subsequently, a solvent is dried out in an oven or the like to form a colored layer of the first color over the entire surface of the black matrix. In general, a color filter comprises pixels of plural colors, so that an undesired portion thereof can be removed by photolithography to form a desired first-color pixel pattern. The pixel film thickness is about 0.5 to 3 µm. This procedure is repeated for pixels for required colors to form pixels of plural colors, thereby forming a color filter. An apparatus and agent used in the process of forming each pixel are preferably the same as those used in the formation of the black matrix, but there should not be any problem if they may be different from each other.

After that, if required, a protective film is laminated. The materials of the protective film include, but not particularly limited to, acrylic resin, epoxy resin, silicone resin and polyimide resin.

In addition, as a method other than those described above, a method so-called backside exposure method and the like may be used, which comprises: previously forming patterned pixels on a transparent substrate; applying a black matrix resist composition thereon; exposing the composition from the transparent substrate side; and using pixels as masks to form a black matrix between the pixels.

Finally, if required, an ITO transparent electrode may be laminated and patterned using any conventional method.

EXAMPLES

Figure 1:
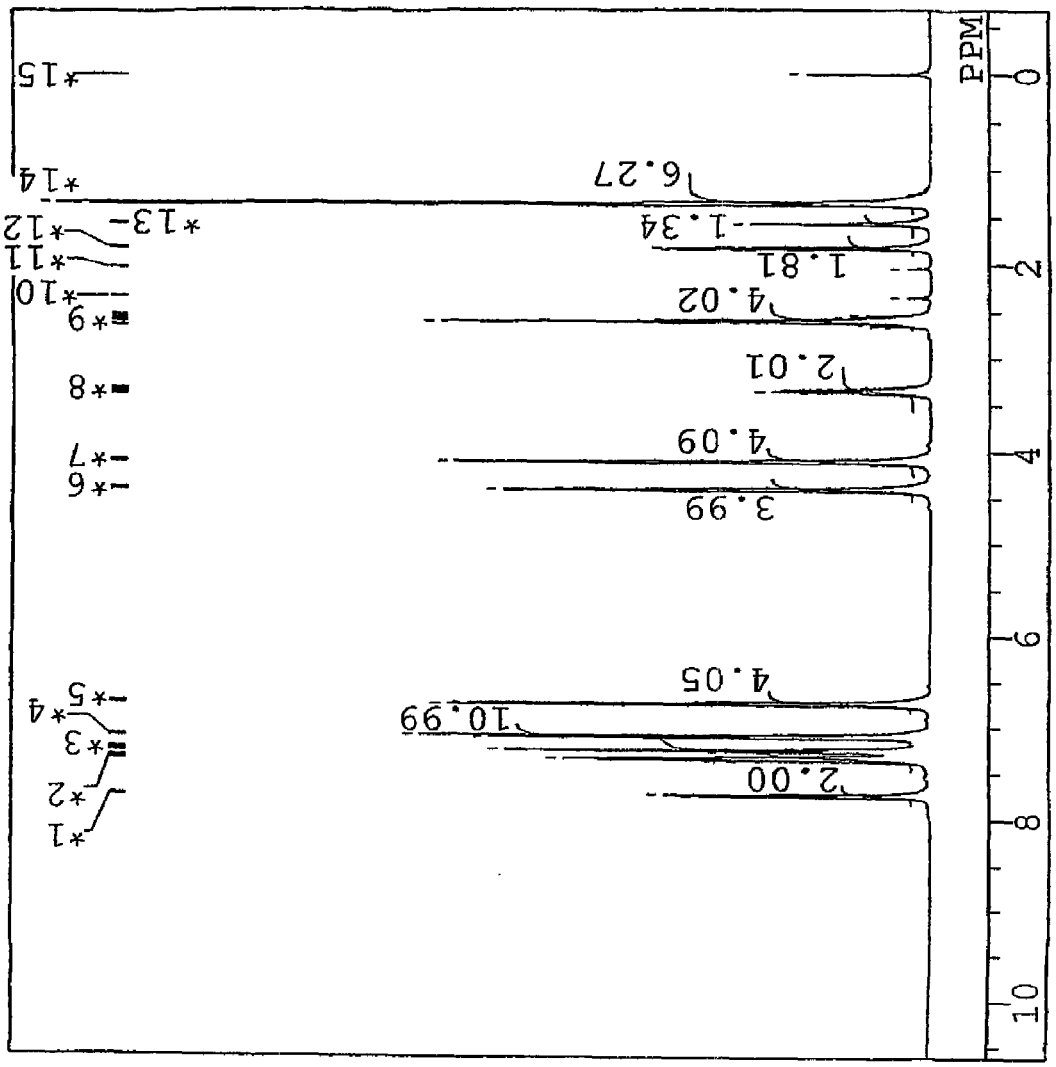
FIG. 1 shows the $^1$H-NMR chart of a thiol (BFMB) 20 μm produced in Synthesis Example 1.

Hereinafter, the present invention will be described in further detail with reference to the synthesis examples of the thiol compounds, photo-radical generator and a binder resin having a carboxyl group on its side chain; the preparation of a black pigment dispersion solution; and the examples and comparative examples of the photosensitive composition and black matrix resist composition of the present invention. However, the present invention should not be construed as being limited by the examples. In the examples, "part" means part by mass, and "%" means % by mass.

Synthesis Example 1

Synthesis of 9,9-bis{4-(3-mercaptobutyloyloxy-ethoxy) phenyl}fluorene (BFMB) (the Compound of Formula (10))

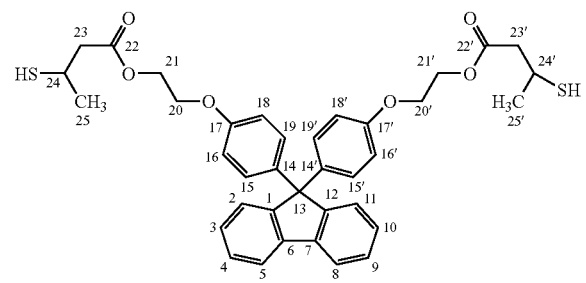

In a 100-ml volume eggplant-shaped flask, 26.97 g (61.5 mmol) of 9,9-bis{4-(2-hydroxyethyl)phenyl}fluorene (produced by Yixing Fine Chemical Co., Ltd.), 15.52 g (129 mmol) of 3-mercapto butyric acid (produced by Yodo Chemical Co., Ltd.), 0.49 g (2.6 mmol) of p-toluene sulfonic acid monohydrate (produced by Junsei Chemicals Co., Ltd.), and 20 g of toluene (produced by Junsei Chemicals Co., Ltd.) were charged, and a Dean-Stark apparatus and a condenser tube were attached to the flask. While being stirred, the contents were heated in an oil bath at a temperature of 140° C. After three hours from the start of the reaction, the reaction mixture was left to cool and neutralized with 100 ml of a 10% aqueous solution of sodium hydrogen carbonate. Further, the reaction mixture was washed with ion-exchanged water three times, and then dehydrated and dried over anhydrous magnesium sulfate (produced by Junsei Chemicals Co., Ltd.). Then, toluene was distilled off and 38.41 g of BFMB (97.1% yield) with a purity of 98.2% was obtained through high-performance liquid chromatography. The resulting BFMB was a colorless transparent liquid with a high viscosity. The BFMB had a compositional formula of $C_{37}H_{38}O_6S_2$ and a molecular weight of 642.89.

Synthesis Example 2

Synthesis of 9,9-bis{4-(2-mercaptoisobutyloyloxy-ethoxy)phenyl}fluorene (BFMIB) (the Compound of Formula (11))

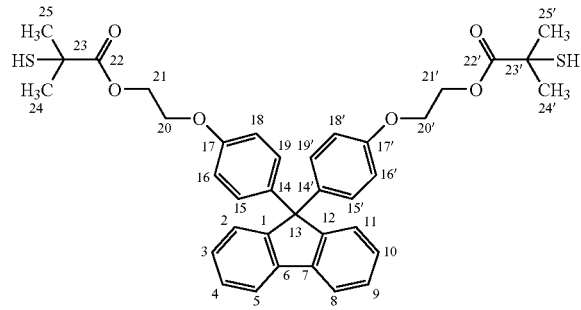

In a 50-ml volume eggplant-shaped flask, 10.00 g (22.8 mmol) of 9,9-bis{4-(2-hydroxyethyl)phenyl}fluorene, 5.76 g (47.9 mmol) of 2-mercaptoisobutyric acid (produced by Yodo Chemical Co., Ltd.), 0.20 g (1.1 mmol) of p-toluene sulfonic acid monohydrate (produced by Junsei Chemicals Co., Ltd.), and 10 g of toluene (produced by Junsei Chemicals Co., Ltd.) were charged, and a Dean-Stark apparatus and a condenser tube were attached to the flask. While being stirred, the contents were heated in an oil bath at a temperature of 140° C. After four hours from the start of the reaction, the reaction mixture was left to cool and neutralized with 50 ml of a 10% aqueous solution of sodium hydrogen carbonate. Further, the reaction mixture was washed with ion-exchanged water three times, and then dehydrated and dried over anhydrous magnesium sulfate (produced by Junsei Chemicals Co., Ltd.). Then, toluene was distilled off and 12.76 g of BFMIB (86.8% yield) with a purity of 90.6% was obtained through high-performance liquid chromatography. The resulting BFMIB was a colorless transparent liquid with a high viscosity. The BFMIB had a compositional formula of $C_{37}H_{38}O_6S_2$ and a molecular weight of 642.89. Then, the BFMIB thus obtained was subjected to column chromatography with silica gel for purification. The silica gel used was Wako Gel C-200 and n-hexane/ethyl acetate=4/1 (by volume ratio) was used as an elution solvent.

The purity of the BFMIB obtained through purification was determined to be 98.5% by high-performance liquid chromatography.

Synthesis Example 3

Synthesis of ethyleneglycol bis(3-mercaptobutylate) (EGMB)

EGMB was synthesized according to the method described in JP 2004-149755 A.

Synthesis Example 4

Synthesis of trimethylolpropane tris(3-mercaptobutylate) (TPMB)

TPMB was synthesized according to the method described in JP 2004-149755 A.

Synthesis Example 5

Synthesis of ethylene glycol bis(2-mercaptoisobutylate) (EGMIB)

EGMIB was synthesized according to the method described in JP 2004-149755 A.

[Analytical Conditions]

The purity of the thiol compound represented by formula (1) obtained by the synthesis was measured using high-performance liquid chromatography shown below.

Column: Shodex 5C84E (manufactured by Showa Denko K.K.),

Eluent composition: acetonitrile/water 3/1 (volume ratio), 2 mM tetra-n-butylammonium perchlorate, Pump: LC-10AD (manufactured by Shimadzu Corp.), Eluent flow rate: 1.0 ml/min, Temperature: 40° C., Detector: UV detector SPD-M10AVP (manufactured by Shimadzu Corp.), and Detection wavelength: 210 nm.

[Conformation Analysis]

(1) BFMB $^1$H-NMR

The $^1$H-NMR chart of BFMB was shown in FIG. 1. The $^1$H-NMR was measured in deuterated chloroform using JNM-AL400 manufactured by JEOL, Ltd. and assignment of the major peak of each chemical shift was performed.

$^1$H-NMR:

1.346, 1.363 ppm: hydrogen atoms of methyl groups of 25, 25', 1.817, 1.834 ppm: hydrogen atoms of mercapto groups, 2.6 ppm: hydrogen atoms of methylene groups of 23, 23', and 3.3 ppm: hydrogen atoms of methine groups of 24, 24'.

$^{13}$C-NMR

Figure 2:
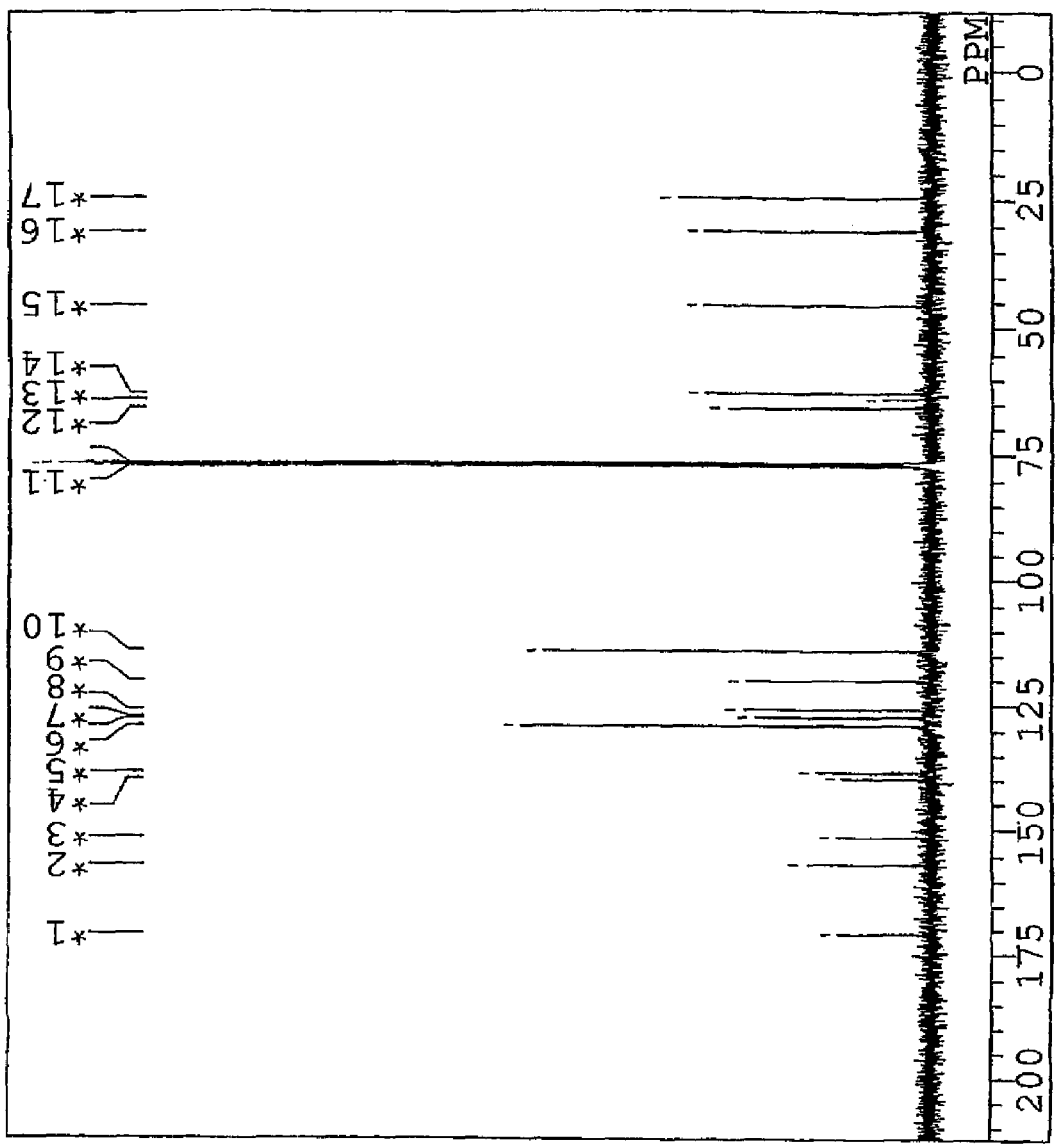
FIG. 2 shows the $^{13}$C-NMR chart of the thiol (BFMB) produced in Synthesis Example 1.

The $^{13}$C-NMR chart of BFMB was shown in FIG. 2. The $^{13}$C-NMR was measured in deuterated chloroform using JNM-AL400 manufactured by JEOL, Ltd. and assignment of the major peak of each chemical shift was performed.

$^{13}$C-NMR:

24.81 ppm: carbon atoms of methyl groups of 25, 25', 31.18 ppm: carbon atoms of methine groups of 24, 24', 45.70 ppm: carbon atoms of methylene groups of 23, 23', and 170.94 ppm: carbon atoms of carbonyl groups of 22, 22'.

(2) BFMIB $^1$H-NMR

Figure 3:
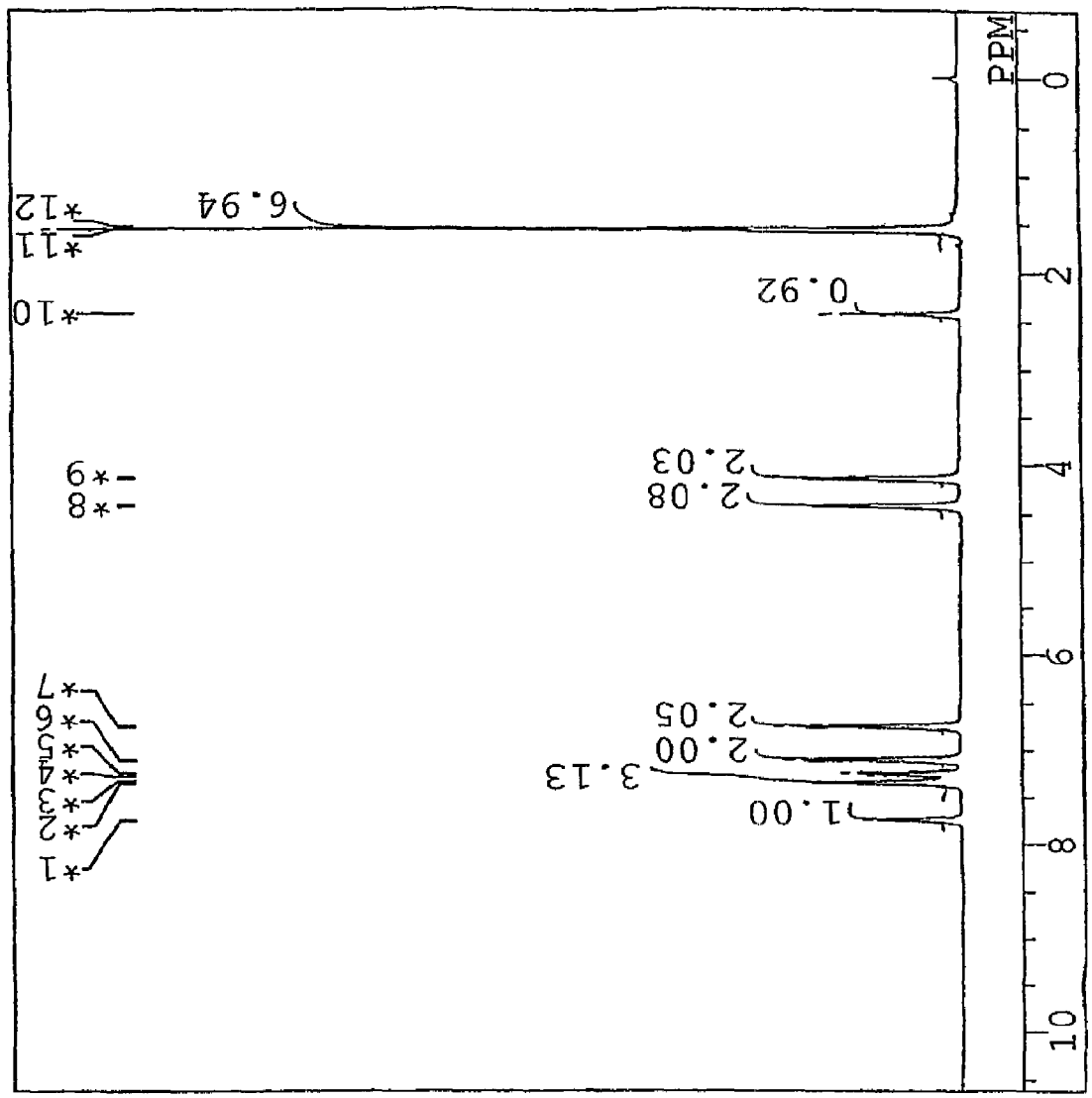
FIG. 3 shows the $^1$H-NMR chart of a thiol (BFMIB) produced in Synthesis Example 2.

The $^1$H-NMR chart of BFMIB was shown in FIG. 3. The $^1$H-NMR was measured in deuterated chloroform using JNM-AL400 manufactured by JEOL, Ltd. and assignment of the major peak of each chemical shift was performed.

$^1$H-NMR:

1.525, 1.552 ppm: hydrogen atoms of methyl groups of 24, 25, 24', 25', and 2.423 ppm: hydrogen atoms of mercapto groups.

$^{13}$C-NMR

Figure 4:
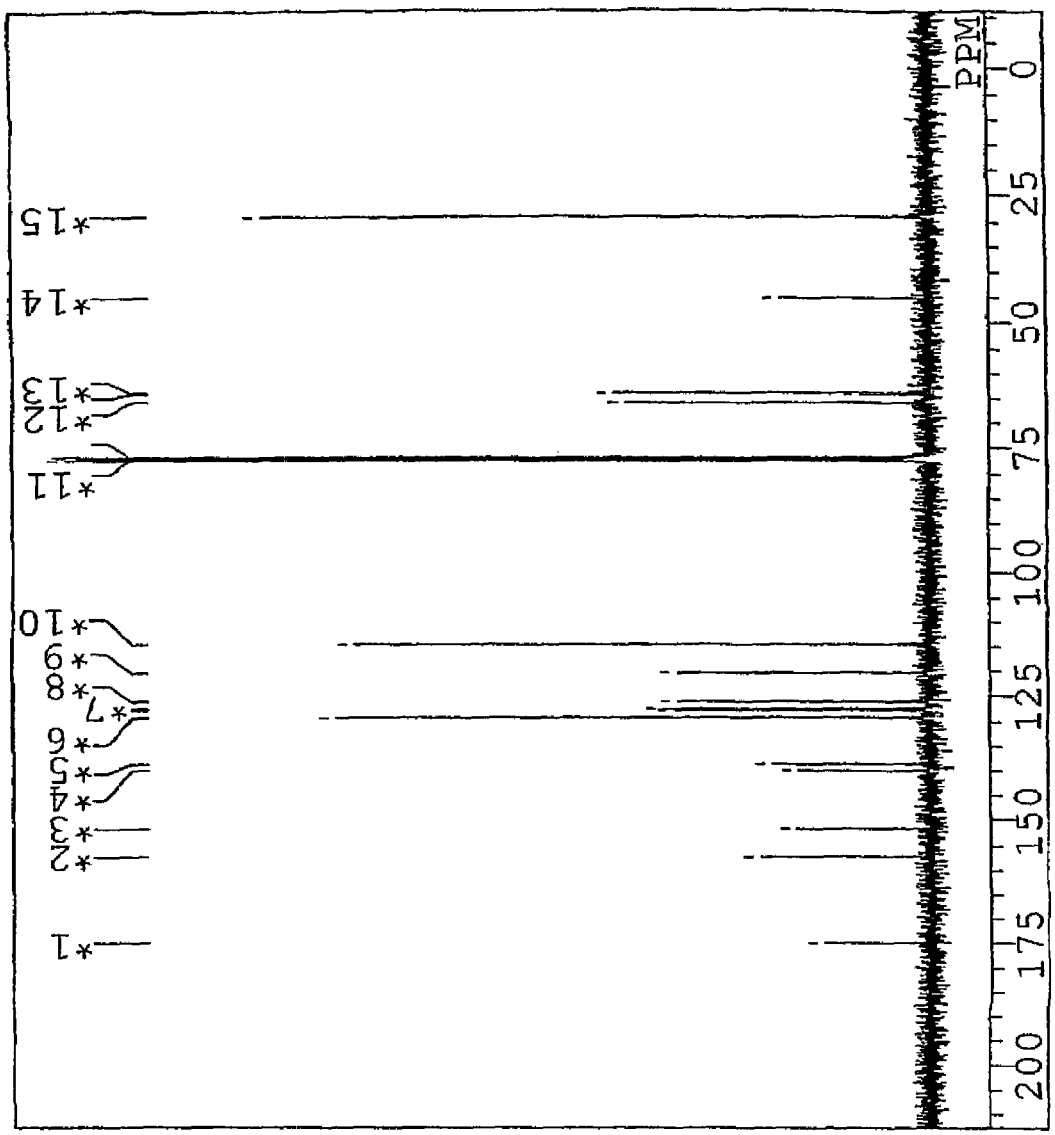
FIG. 4 shows the $^{13}$C-NMR chart of the thiol (BFMIB) produced in Synthesis Example 2.

The $^{13}$C-NMR chart of BFMIB was shown in FIG. 4. The $^{13}$C-NMR was measured in deuterated chloroform using JNM-AL400 manufactured by JEOL, Ltd. and assignment of the major peak of each chemical shift was performed.

$^{13}$C-NMR:

29.20 ppm: carbon atoms of methyl groups of 24, 25, 24', 25', 45.08 ppm: carbon atoms of methine groups of 23, 23', and 175.05 ppm: carbon atoms of carbonyl groups of 22, 22'.

(2) Synthesis of Photo-radical Generator

Synthesis Example 6

2,2'-bis(2-chlorophenyl)-4,4',5,5'-tetrakis(4-methylphenyl)-1,2'-biimidazole (Hereinafter, Abbreviated as MHABI)

In a 1-L volume eggplant-shaped flask, 27.50 g (115 mmol) of 4,4'-dimethylbenzil (produced by Tokyo Kasei Kogyo Co., Ltd.), 16.25 g (116 mmol) of o-chlorbenzaldehyde (produced by Tokyo Kaseii Kogyo Co., Ltd.), 69.45 g (901 mmol) of ammonium acetate (produced by Junsei Chemicals Co., Ltd.) and 450 g of acetic acid (produced by Junsei Chemicals Co., Ltd.) were charged.

While being stirred, the contents were heated at 117° C. and reacted for five hours. After having been cooled, the reaction liquid was gradually poured into 2 L of deionized water being stirred, causing precipitation of 2-(2-chlorophenyl)-4,5-bis(4-methylphenyl) imidazole. Subsequently, 2-(2-chlorophenyl)-4,5-bis(4-methylphenyl) imidazole was filtrated and washed with water, and then dissolved in 500 g of methylene chloride (produced by Junsei Chemicals Co., Ltd.), followed by being charged into a 2-L volume four-neck flask and cooled to 5 to 10° C. In this solution, a mixture of 117.6 g (357 mmol) of potassium ferricyanide (produced by Junsei Chemicals Co., Ltd.), 44.7 g of sodium hydroxide (produced by Junsei Chemicals Co., Ltd.) and 600 g of deionized water was gradually added for one hour while stirring, and then reacted for 18 hours at room temperature. The reaction mixture was washed with deionized water three times, and then dehydrated over about 50 g of anhydrous magnesium sulfate (produced by Junsei Chemicals Co., Ltd.). Then, methylene chloride was distilled off under reduced pressure, resulting in crystals of MHABI. The MHABI was re-crystallized through ethanol (produced by Junsei Chemicals Co., Ltd.) and then filtrated and dried, thereby obtaining 36.5 g of light-yellow crystal (88.7% yield).

(3) Synthesis of Binder Resin having Carboxyl Group on Side Chain Synthesis Example 7: Synthesis of EP-1

185 g of Epicoat 1004 (bisphenol A type epoxy resin, produced by Japan Epoxy Resin Co., Ltd., epoxy equivalent of 925), 14.4 g of acrylic acid, 0.20 g of hydroquinone and 197 g of diethyleneglycol monoethylether acetate (hereinafter, abbreviated as DGEA, produced by Daicel Chemical Industries, Ltd.) were charged and heated to 95° C. After it has been confirmed that the mixture had been dissolved uniformly, 2.0 g of triphenylphosphine was charged and the whole was heated to 100° C. to react for about 30 hours, thereby obtaining a reaction product having an acid value of 0.5 mgKOH/g. The reaction product was provided with 96.0 g of tetrahydrophthalic anhydride (produced by New Japan Chemical Co., Ltd.) and the whole was heated to 90° C. to react for six hours, followed by confirming the disappearance of absorbance of the acid anhydride in IR, resulting in epoxy acrylate resin EP-1 having a solid acid value of 119 mgKOH/g and a solid concentration of 60%.

Synthesis Example 8

Synthesis of EP-2

185 g of Epicoat 1004 (bisphenol A type epoxy resin, epoxy equivalent of 925; produced by Japan Epoxy Resin Co., Ltd.), 14.4 g of acrylic acid, 0.20 g of hydroquinone, and 197 g of diethyleneglycol monoethylether acetate (DGEA) (produced by Daicel Chemical Industries, Ltd.) were charged and heated to 95° C. After it has been confirmed that the mixture had been dissolved uniformly, 2.0 g of triphenylphosphine was charged and the whole was heated to 100° C. to react for about 30 hours, thereby obtaining a reaction product having an acid value of 0.5 mgKOH/g. The reaction product was provided with 70.0 g of tetrahydrophthalic anhydride (produced by New Japan Chemical Co., Ltd.) and the whole was heated to 90° C. to react for about six hours, followed by confirming the disappearance of absorbance of the acid anhydride in an infrared absorption spectrum (IR), resulting in epoxy acrylate resin EP-2 having a solid acid value of 95 mgKOH/g and a solid concentration of 60%.

Synthesis Example 9

Synthesis of AP-1

In a four-neck flask attached with a dropping funnel, a thermometer, a condenser tube, and a stirring device, 37.5 g of methacrylic acid (MA) (produced by Kyoeisha Chemical Co., Ltd.), 19.0 g of methyl methacrylate (MMA) (produced by Kyoeisha Chemical Co., Ltd., hereinafter abbreviated as MMA), 18.5 g of n-butyl methacrylate (BMA) (produced by Kyoeisha Chemical Co., Ltd.), 0.75 g of 2-mercaptoethanol (produced by Wako Pure Chemical Industry Co., Ltd.), and 225.0 g of propyleneglycol methylether (PGM) (produced by Tokyo Kasei Kogyo Co., Ltd.) were charged, and the inside of the four-neck flask was then replaced with nitrogen gas for one hour. Furthermore, the flask was heated up to 90° C. in an oil bath, and thereto a mixture solution of 37.5 g of MA, 19.0 g of MMA, 18.5 g of BMA, 0.75 g of 2-mercaptoethanol, 225.0 g of PGM and 3.2 g of 2,2'-azobis isobutyronitrile (AIBN) (produced by Wako Pure Chemical Industry, Co., Ltd.) was then gradually dropped for one hour. After three hours of polymerization, the resultant was heated up to 100° C. and then mixed with a mixture solution of 1.0 g of AIBN and 15.0 g of propyleneglycol methyletheracetate (PMA) (produced by Daicel Chemical Industries, Ltd.), followed by carrying out additional 1.5-hour polymerization and then standing to cool. Subsequently, the inside of the four-neck flask was replaced with flesh air and then the flask was added with 61.5 parts by mass of glycidyl methacrylate (GMA) (produced by Mitsubishi Rayon Co., Ltd.), 3.6 g of tetra-n-butylammonium bromide (TBAB) (produced by Tokyo Kasei Kogyo Co., Ltd.), and 0.15 g of methoquinone (produced by Junsei Chemical, Co., Ltd.) to carry out a reaction for eight hours at 80° C., thereby adding GMA to the carboxyl group of acrylic copolymer. Consequently, GMA-addition acrylic copolymer (AP-1) was obtained. The solid concentration of AP-1 was 30.5%, the solid acid value thereof was 116 mgKOH/g, and the weight-average molecular weight thereof in terms of polystyrene measured by GPC was 14,000.

(4) Preparation of Pigment Dispersion Solution 1 Used for Photosensitive Composition In a 300-ml volume stainless steel can, 1.98 g of Ajisper PB822 (pigment dispersant, produced by Ajinomoto-Fine-Techno Co., Inc.) was dissolved with 113.5 g propyleneglycol monomethyletheracetate (hereinafter, abbreviated as PMA, produced by Daicel Chemical Industries, Ltd.), and then mixed with 12.54 g of EP-1, 15.0 g of Special Black 350 (carbon black, produced by Degussa Co., Ltd.) and 15.0 g of 13M-C (titanium black, produced by Mitsubishi Materials Corporation). Subsequently, 200 g of zirconium beads of 0.65 mm in diameter was added to the reaction mixture and the whole was then subjected to dispersion treatment for three hours with a paint conditioner (produced by Asada Iron Works Co., Ltd.). The above pigment dispersion solution was filtrated through filter paper of 0.8 μm in pore size to prepare a black pigment dispersion solution.

(5) Preparation of Black Pigment Dispersion Solution Used for Black Matrix Resist Composition Dispersion Solution 2:

In a mixture solvent of 1,874 g of cyclohexanone (CH) and 1,874 g of PMA, 57 g of a dispersant Ajisper PB822 (produced by Ajinomoto-Fine-Techno Co., Inc.) was dissolved and 317 g of EP-1 (solid content: 190 g) was then mixed. Subsequently, 439 g of carbon black Special Black 350 (SB 350) (produced by Degussa Co., Ltd.) and 439 g of titanium black 13M-C (produced by Mitsubishi Materials Corporation) as black pigments were mixed, followed by prefixing with a disperser. Furthermore, the mixture solution was dispersed using a continuous annular type beads mill (trade name: SpikeMill Type: SHG-4C, manufactured by Inoue. Manufacturing Co., Ltd.). The beads used were zirconium beads of 0.40 mm in diameter and the packed percentage of the beads in the vessel was 80% by volume. The peripheral speed of a rotor was set to 12 m/second, the discharge rate of the black pigment dispersion solution was set to 1 litter/minute, and temperature was set to about 30° C. The retaining period of the black pigment dispersion solution was set to six minutes (driving time: one hour). A dispersion solution 2 was obtained according to the above method.

Dispersion Solutions 3 and 4

Dispersion solutions 3 and 4 were prepared from the compositions shown in Table 1 by the same method as that of the dispersion solution 2.

TABLE 1

|  | Dispersant 2 | | | Dispersant 3 | | | Dispersant 4 | | |
|---|---|---|---|---|---|---|---|---|---|
|  | Blending amount (g) | Composition of Solids (g) | Composition ratio of solids (mass %) | Blending amount (g) | Composition of Solids (g) | Composition ratio of solids (mass %) | Blending amount (g) | Composition of Solids (g) | Composition ratio of solids (mass %) |
| Black pigment dispersant | | | | | | | | | |
| Special Black 350 *1 | 439 | 439 | 39.0 | 439 | 439 | 39.0 | 439 | 439 | 39.0 |
| 13M-C *2 | 439 | 439 | 39.0 | 439 | 439 | 39.0 | 439 | 439 | 39.0 |
| Ajisper PB822 *3 | 57 | 57 | 5.1 | 57 | 57 | 5.1 | 57 | 57 | 5.1 |
| EP-1 | 317 | 190 | 16.9 | — | — | — | — | — | — |
| EP-2 | — | — | — | 317 | 190 | 16.9 | — | — | — |
| AP-1 | — | — | — | — | — | — | 623 | 190 | 16.9 |

TABLE 1-continued

| | Dispersant 2 | | | Dispersant 3 | | | Dispersant 4 | | |
|---|---|---|---|---|---|---|---|---|---|
| | Blending amount (g) | Composition of Solids (g) | Composition ratio of solids (mass %) | Blending amount (g) | Composition of Solids (g) | Composition ratio of solids (mass %) | Blending amount (g) | Composition of Solids (g) | Composition ratio of solids (mass %) |
| Organic solvent | | | | | | | | | |
| PMA *4 | 1874 | — | — | 1874 | — | — | 1721 | — | — |
| CH *5 | 1874 | — | — | 1874 | — | — | 1721 | — | — |
| TOTAL | 5000 | 1125 | 100.0 | 5000 | 1125 | 100.0 | 5000 | 1125 | 100.0 |

*1 Carbon black produced by Degussa AG
*2 Titanium black produced by Mitsubishi Materials Corporation
*3 Pigment dispersant produced by Ajinomoto-Fine-Techno Co., Inc.
*4 Propyleneglycol monomethyletheracetate produced by Daicel Chemical Industries, Ltd.
*5 Cyclohexanone produced by Wako Pure Chemical Industries, Ltd.

(6) Preparation of Photosensitive Composition

Photosensitive compositions of Examples 1 to 3 and Comparative Examples 1 to 3 were prepared according to the compositions listed in Tables 2 and 3.

(7) Preparation of Black Matrix Resist Composition

Black matrix resist compositions of Examples 4 to 9 and Comparative Examples 4 to 6 were prepared from the compositions listed in Tables 4 to 6.

(8) Evaluation of Photosensitive Composition and Black Matrix Resist Composition

[Appropriate Developing Time]

Each of the photosensitive compositions of Examples 1 to 3 and Comparative Examples 1 to 3 and each of the black matrix resist compositions of Examples 4 to 9 and Comparative Examples 4 to 6 was applied to a glass substrate (dimensions: 100×100×1 mm) to form a dry film having a thickness of about 1 μm by means of a spin coater and left alone for five minutes at room temperature, followed by drying the solvent for three minutes at 90° C. Furthermore, the glass substrate was exposed at 100 mj/cm² with an exposure device equipped with a super-high pressure mercury lamp (trade name: MultiLight ML-251A/B, manufactured by Ushio Inc.) through a photomask made of quartz for photo-curing. The exposure value was measured using a UV accumulated-amount meter (trade name: UIT 150, manufactured by Usio Inc., light-receiving portion: UVD-S365). In addition, the quartz photomask obtained had a pattern having 4, 6, 8, 10, 20, 50 and 100 μm of line/space, and a pattern having lines of 4, 6, 8, 10, 20, 50 and 100 μm and spaces of all equal to 50 μm.

A film of the exposed and cured photosensitive composition was further subjected to alkaline development with time variation with an aqueous solution (21° C.) containing 0.25% Developer 9033 (produced by Shipley Far East., Co., Ltd.) provided as an alkaline developer containing potassium carbonate and 0.03% sodium dodecylbenzenesulfonate (produced by Tokyo Kasei Kogyo Co., Ltd.) by a spin developer (AD-1200, produced by Takizawa Industries, Co., Ltd.). After that, the line width of each line formed by exposure was measured by an optical microscope (VH-Z250, manufactured by Keyence Corp.). The appropriate developing time was defined as a time period for making the line width to about 20 μm for the line obtained by the photo-curing of a portion wherein the width of the photomask lines is 20 μm and that of the space is 50 μm.

[Resolution]

Each of the photosensitive compositions of Examples 1 to 3 and Comparative Examples 1 to 3 and each of the black matrix resist compositions of Examples 4 to 9 and Comparative Examples 4 to 6 was subjected to alkaline development by the same way as mentioned in the above appropriate developing time with an appropriate developing time after the drying of the solvent and the exposure. The minimum line width, in which patterns of line/space as the same patterns as those of photomasks were formed by the exposure, was measured using an optical microscope (VH-Z250, manufactured by Keyence Corp.). The results are shown in Tables 2 to 6.

[Development Latitude]

Each of the photosensitive compositions of Examples 1 and 2 and Comparative Examples 1 to 3 and each of the black matrix resist compositions of Examples 4 to 9 and Comparative Examples 4 to 6 was subjected to alkaline development by the same way as mentioned in the above appropriate developing time for an appropriate developing time or the appropriate time plus 30 seconds after the drying of the solvent and the exposure. The minimum line width on part of patterns of the photomask having lines of 4, 6, 8, 10, 20, 50, and 100 μm and spaces of all equal to 50 μm was measured using an optical microscope (VH-Z250, manufactured by Keyence Corp.). The results are shown in Tables 2 to 6.

[OD Value (Optical Density)]

Each of the black matrix resist compositions of Examples 4 to 9 and Comparative Examples 4 to 6 was spin-coated on a glass substrate (100×100 mm in dimensions) and then dried at room temperature for five minutes, followed by drying a solvent at 90° C. for three minutes. The resultant was exposed at 100 mj/cm² by an ultra-high pressure mercury lamp and then post-baked at 230° C. for 60 minutes. The resulting glass substrate applied with resist was used and the OD value thereof was measured. The OD value was determined from a standard curve made by measuring a transmission factor at 550 nm on a standard board of the known OD value. Subsequently, the resist-applied glass substrate of each of Examples and Comparative Examples was subjected to the measurement of transmission factor at 550 nm to calculate the OD value. The results are shown in Tables 4 to 6.

TABLE 2

| | | Example 1 | | Example 2 | | Example 3 | |
|---|---|---|---|---|---|---|---|
| | | Blending amount (g) | Composition ratio of solids (mass %) | Blending amount (g) | Composition ratio of solids (mass %) | Blending amount (g) | Composition ratio of solids (mass %) |
| Component of photosensitive composition | Black pigment dispersant (Special Black 350) *1 | 65.0 (6.18) | 84.4 (32.1) | 65.0 (6.18) | 84.4 (32.1) | 65.0 (6.18) | 84.4 (32.1) |
| | (13M-C) *2 | (6.18) | (32.1) | (6.18) | (32.1) | (6.18) | (32.1) |
| | (Ajisper PB822) *3 | (0.81) | (4.2) | (0.81) | (4.2) | (0.81) | (4.2) |
| | (EP-1) | (3.09) | (16.0) | (3.09) | (16.0) | (3.09) | (16.0) |
| | (PMA) *4 | (46.68) | (—) | (46.68) | (—) | (46.68) | (—) |
| | (DGEA) *5 | (2.06) | (—) | (2.06) | (—) | (2.06) | (—) |
| | Compound having an ethylenically unsaturated group | | | | | | |
| | Light-Acrylate BP-4EA *6 | 0.50 | 2.6 | 0.20 | 1.0 | 0.50 | 2.6 |
| | Aronix M-400 *7 | 0.50 | 2.6 | 0.50 | 2.6 | 0.50 | 2.6 |
| | Photopolymerization initiator system | | | | | | |
| | EMK *8 | 0.30 | 1.5 | 0.30 | 1.5 | 0.30 | 1.5 |
| | MHABI | 1.00 | 5.2 | — | — | 1.00 | 5.2 |
| | Irgacure 907 *9 | — | — | 1.00 | 5.2 | — | — |
| | Thiol compound | | | | | | |
| | BFMB | 0.70 | 3.6 | 1.00 | 5.2 | — | — |
| | BFMIB | — | — | — | — | 0.70 | 3.6 |
| | Organic solvent | | | | | | |
| | Cyclohexanone | 31.98 | — | 31.98 | — | 31.98 | — |
| | Leveling agent | | | | | | |
| | Megafac R08 *10 | 0.02 | 0.1 | 0.02 | 0.1 | 0.02 | 0.1 |
| | TOTAL | 100.0 | 100.0 | 100.0 | 100.0 | 100.0 | 100.0 |
| Evaluation items | Appropriate developing time (sec) | 35 | | 25 | | 40 | |
| | Resolution (line/space μm) | 6 | | 6 | | 8 | |
| | Development latitude (μm) Appropriate developing time | 4 | | 4 | | 6 | |
| | Appropriate developing time + 30 sec | 6 | | 6 | | 6 | |

*1 Carbon black produced by Degussa AG
*2 Titanium black produced by Mitsubishi Materials Corporation
*3 Pigment dispersant produced by Ajinomoto-Fine-Techno Co., Inc.
*4 Propyleneglycol monomethyletheracetate produced by Daicel Chemical Industries, Ltd.
*5 Diethyleneglycol monomethyletheracetate produced by Daicel Chemical Industries, Ltd.
*6 Diacrylate of 4-mol EO adduct of bisphenol A produced by Kyoeisha Chemical Co., Ltd.
*7 Dipentaerythritol hexacrylate produced by Toagosei Co., Ltd.
*8 N,N-bis(diethylamino)benzophenone produced by Hodogaya Chemical Co., Ltd.
*9 2-methyl-1-[4-(methylthio)phenyl]-2-morpholinopropan-1-one, produced by Chiba Specialty Chemicals K.K.
*10 Fluorine compound produced by Dainippon Ink and Chemicals, Incorporated

TABLE 3

| | | Comp. Example 1 | | Comp. Example 2 | | Comp. Example 3 | |
|---|---|---|---|---|---|---|---|
| | | Blending amount (g) | Composition ratio of solids (mass %) | Blending amount (g) | Composition ratio of solids (mass %) | Blending amount (g) | Composition ratio of solids (mass %) |
| Component of photosensitive composition | Black pigment dispersant (Special Black 350) | 65.0 (6.18) | 84.4 (32.1) | 65.0 (6.18) | 84.4 (32.1) | 65.0 (6.18) | 84.4 (32.1) |
| | (13M-C) | (6.18) | (32.1) | (6.18) | (32.1) | (6.18) | (32.1) |
| | (Ajisper PB822) | (0.81) | (4.2) | (0.81) | (4.2) | (0.81) | (4.2) |
| | (EP-1) | (3.09) | (16.0) | (3.09) | (16.0) | (3.09) | (16.0) |
| | (PMA) | (46.68) | (—) | (46.68) | (—) | (46.68) | (—) |
| | (DGEA) | (2.06) | (—) | (2.06) | (—) | (2.06) | (—) |

TABLE 3-continued

|  |  | Comp. Example 1 | | Comp. Example 2 | | Comp. Example 3 | |
| --- | --- | --- | --- | --- | --- | --- | --- |
|  |  | Blending amount (g) | Composition ratio of solids (mass %) | Blending amount (g) | Composition ratio of solids (mass %) | Blending amount (g) | Composition ratio of solids (mass %) |
|  | Compound having an ethylenically unsaturated group |  |  |  |  |  |  |
|  | Light-Acrylate BP-4EA | 0.50 | 2.6 | 0.50 | 2.6 | 0.50 | 2.6 |
|  | Aronix M-400 | 0.50 | 2.6 | 0.50 | 2.6 | 0.50 | 2.6 |
|  | Photopolymerization initiator system |  |  |  |  |  |  |
|  | EMK | 0.30 | 1.5 | 0.30 | 1.5 | 0.30 | 1.5 |
|  | MHABI | 1.00 | 5.2 | 1.00 | 5.2 | 1.00 | 5.2 |
|  | Thiol compound |  |  |  |  |  |  |
|  | EGMB | 0.70 | 3.6 | — | — | — | — |
|  | EGMIB | — | — | 0.70 | 3.6 | — | — |
|  | TPMB | — | — | — | — | 0.70 | 3.6 |
|  | Organic solvent |  |  |  |  |  |  |
|  | Cyclohexanone | 31.98 | — | 31.98 | — | 31.98 | — |
|  | Leveling agent |  |  |  |  |  |  |
|  | Megafac R08 | 0.02 | 0.1 | 0.02 | 0.1 | 0.02 | 0.1 |
|  | TOTAL | 100.0 | 100.0 | 100.0 | 100.0 | 100.0 | 100.0 |
| Evaluation items | Appropriate developing time (sec) | 25 | | 30 | | 30 | |
|  | Resolution (line/space μm) | 6 | | 6 | | 4 | |
| Development latitude (μm) | Appropriate developing time | 6 | | 6 | | 4 | |
|  | Appropriate developing time + 30 sec | 50 | | 50 | | 20 | |

TABLE 4

|  | Example 4 | | Example 5 | | Example 6 | |
| --- | --- | --- | --- | --- | --- | --- |
|  | Blending amount (g) | Composition of Solids (mass %) | Blending amount (g) | Composition of Solids (mass %) | Blending amount (g) | Composition of Solids (mass %) |
| Black matrix resist composition |  |  |  |  |  |  |
| Black Pigment | 70.6 | 83.6 | 70.6 | 83.6 | 70.6 | 83.6 |
| Dispersant |  |  |  |  |  |  |
| (Special Black 350) | (6.20) | (32.6) | (6.20) | (32.6) | (6.20) | (32.6) |
| (13M-C) | (6.20) | (32.6) | (6.20) | (32.6) | (6.20) | (32.6) |
| (AJISPER PB822) | (0.81) | (4.3) | (0.81) | (4.3) | (0.81) | (4.3) |
| (EP-1) | (2.68) | (14.1) | — | (-) | — | (-) |
| (EP-2) | — | (-) | (2.68) | (14.1) | — | (-) |
| (AP-1) | — | (-) | — | (-) | (2.68) | (14.1) |
| (PMA) | (26.47) | (-) | (26.47) | (-) | (24.30) | (-) |
| (DGEA) *6 | (1.80) | (-) | (1.80) | (-) | — | (-) |
| (CH) | (26.47) | (-) | (26.47) | (-) | (24.30) | (-) |
| (PGM) *7 | — | (-) | — | (-) | (6.11) | (-) |
| Compound having an ethylenically unsaturated group |  |  |  |  |  |  |
| LIGHT-ACRYLATE BP-4EA *8 | 0.54 | 2.8 | 0.54 | 2.8 | 0.54 | 2.8 |
| ARONIX M-400 *9 | 0.55 | 2.9 | 0.55 | 2.9 | 0.55 | 2.9 |
| Photopolymerization initiator system |  |  |  |  |  |  |
| EMK *10 | 0.30 | 1.6 | 0.30 | 1.6 | 0.30 | 1.6 |
| MHABI | 1.00 | 5.3 | 1.00 | 5.3 | 1.00 | 5.3 |

TABLE 4-continued

|  | Example 4 | | Example 5 | | Example 6 | |
| --- | --- | --- | --- | --- | --- | --- |
|  | Blending amount (g) | Composition of Solids (mass %) | Blending amount (g) | Composition of Solids (mass %) | Blending amount (g) | Composition of Solids (mass %) |
| Thiol compound |  |  |  |  |  |  |
| BFMB | 0.70 | 3.7 | 0.70 | 3.7 | 0.70 | 3.7 |
| BFMIB | — | — | — | — | — | — |
| Organic solvent |  |  |  |  |  |  |
| CH | 26.29 | — | 26.29 | — | 26.29 | — |
| Leveling agent |  |  |  |  |  |  |
| MEGAFAC R08 *11 | 0.02 | 0.1 | 0.02 | 0.1 | 0.02 | 0.1 |
| Total | 100.0 | 100.0 | 100.0 | 100.0 | 100.0 | 100.0 |
| Evaluation items |  |  |  |  |  |  |
| Appropriate developing time (sec) | 30 | | 35 | | 25 | |
| Resolution (line/space μm) | 6 | | 6 | | 6 | |
| Development latitude(μm) Appropriate developing time | 4 | | 4 | | 8 | |
| Appropriate developing time + 30 seconds | 6 | | 6 | | 10 | |
| OD value (/μm) | 5.1 | | 5.1 | | 5.3 | |

*6: Diethylene glycol monomethyl ether acetate produced by Daicel Chemical Industries, Ltd.
*7: Propylene glycol monomethyl ether acetate produced by Daicel Chemical Industries, Ltd.
*8: Diacrylate of 4-mol EO adduct bisphenol A produced by Kyoeisha Chemical Co., Ltd.
*9: Dipentaerythritol hexaacrylate produced by Toagosei Co., ltd.
*10: 4,4'-Bis(N,N-diethylamino)benzophenone produced by HODOGAYA CHEMICAL Co., Ltd.
*11: Fluorine compound produced by DAINIPPON INK AND CHEMICALS, INC.

TABLE 5

|  | Example 7 | | Example 8 | | Example 9 | |
| --- | --- | --- | --- | --- | --- | --- |
|  | Blending amount (g) | Composition of Solids (mass %) | Blending amount (g) | Composition of Solids (mass %) | Blending amount (g) | Composition of Solids (mass %) |
| Black matrix resist composition |  |  |  |  |  |  |
| Black Pigment Dispersant | 70.6 | 83.6 | 70.6 | 83.6 | 70.6 | 83.6 |
| (Special Black 350) | (6.20) | (32.6) | (6.20) | (32.6) | (6.20) | (32.6) |
| (13M-C) | (6.20) | (32.6) | (6.20) | (32.6) | (6.20) | (32.6) |
| (AJISPER PB822) | (0.81) | (4.3) | (0.81) | (4.3) | (0.81) | (4.3) |
| (EP-1) | (2.68) | (14.1) | (2.68) | (14.1) | (2.68) | (14.1) |
| (PMA) | (26.47) | (-) | (26.47) | (-) | (26.47) | (-) |
| (DGEA) | (1.80) | (-) | (1.80) | (-) | (1.80) | (-) |
| (CH) | (26.47) | (-) | (26.47) | (-) | (26.47) | (-) |
| Compound having an ethylenically unsaturated group |  |  |  |  |  |  |
| LIGHT-ACRYLATE BP-4EA | 0.54 | 2.8 | 0.54 | 2.8 | — | (-) |
| ARONIX M-400 | 0.55 | 2.9 | 0.55 | 2.9 | 0.55 | 2.9 |
| LIGHT-ACRYLATE DPC-A *12 | — | (-) | — | (-) | 0.54 | 2.8 |
| Photopolymerization initiator system |  |  |  |  |  |  |
| EMK | 0.30 | 1.6 | 0.30 | 1.6 | 0.30 | 1.6 |
| MHABI | 1.00 | 5.3 | — | — | 1.00 | 5.3 |
| Irgacure 907 *13 | — | — | 1.00 | 5.3 | — | (-) |

TABLE 5-continued

|  | Example 7 | | Example 8 | | Example 9 | |
|---|---|---|---|---|---|---|
|  | Blending amount (g) | Composition of Solids (mass %) | Blending amount (g) | Composition of Solids (mass %) | Blending amount (g) | Composition of Solids (mass %) |
| Thiol compound |  |  |  |  |  |  |
| BFMB | — | — | 0.70 | 3.7 | 0.70 | 3.7 |
| BFMIB | 0.70 | 3.7 | — | — | — | — |
| Organic solvent |  |  |  |  |  |  |
| CH | 26.29 | — | 26.29 | — | 26.29 | — |
| Leveling agent |  |  |  |  |  |  |
| MEGAFAC R08 | 0.02 | 0.1 | 0.02 | 0.1 | 0.02 | 0.1 |
| Total | 100.0 | 100.0 | 100.0 | 100.0 | 100.0 | 100.0 |
| Evaluation result |  |  |  |  |  |  |
| Appropriate developing time (second) | 30 | | 20 | | 25 | |
| Resolution (line/space μm) | 8 | | 6 | | 8 | |
| Development latitude (μm) | 6 | | 4 | | 8 | |
| Appropriate developing time |  |  |  |  |  |  |
| Appropriate developing time + 30 seconds | 8 | | 8 | | 10 | |
| OD value (/μm) | 5.1 | | 5.2 | | 5.3 | |

*12 dimethylol tricyclo decanediacrylate produced by Kyoeisha Chemical Co., Ltd.
*13 2-methyl-1-[4-(methylthio)phenyl]-2-morpholino propane-1-one produced by Ciba Specialty Chemicals K.K.

TABLE 6

|  | Comparative Example 3 | | Comparative Example 4 | | Comparative Example 5 | |
|---|---|---|---|---|---|---|
|  | Blending amount (g) | Composition of Solids (mass %) | Blending amount (g) | Composition of Solids (mass %) | Blending amount (g) | Composition of Solids (mass %) |
| Comparitive Black matrix resist composition |  |  |  |  |  |  |
| Black Pigment Dispersant | 70.6 | 83.6 | 70.6 | 83.6 | 70.6 | 83.6 |
| (Special Black 350) | (6.20) | (32.6) | (6.20) | (32.6) | (6.20) | (32.6) |
| (13M-C) | (6.20) | (32.6) | (6.20) | (32.6) | (6.20) | (32.6) |
| (AJISPER PB822) | (0.81) | (4.3) | (0.81) | (4.3) | (0.81) | (4.3) |
| (EP-1) | (2.68) | (14.1) | (2.68) | (14.1) | (2.68) | (14.1) |
| (PMA) | (26.47) | (-) | (26.47) | (-) | (26.47) | (-) |
| (DGEA) | (1.80) | (-) | (1.80) | (-) | (1.80) | (-) |
| (CH) | (26.47) | (-) | (26.47) | (-) | (26.47) | (-) |
| Compound having an ethylenically unsaturated group |  |  |  |  |  |  |
| LIGHT-ACRYLATE BP-4EA | 0.54 | 2.8 | 0.54 | 2.8 | 0.54 | 2.8 |
| ARONIX M-400 | 0.55 | 2.9 | 0.55 | 2.9 | 0.55 | 2.9 |
| Photopolymerization initiator system |  |  |  |  |  |  |
| EMK | 0.30 | 1.6 | 0.30 | 1.6 | 0.30 | 1.6 |
| MHABI | 1.00 | 5.3 | 1.00 | 5.3 | 1.00 | 5.3 |
| Thiol compound |  |  |  |  |  |  |
| EGMB | 0.70 | 3.7 | — | (-) | — | (-) |
| TPMB | — | (-) | 0.70 | 3.7 | — | (-) |
| EGMIB | — | (-) | — | (-) | 0.70 | 3.7 |

TABLE 6-continued

|  | Comparative Example 3 | | Comparative Example 4 | | Comparative Example 5 | |
|---|---|---|---|---|---|---|
|  | Blending amount (g) | Composition of Solids (mass %) | Blending amount (g) | Composition of Solids (mass %) | Blending amount (g) | Composition of Solids (mass %) |
| Organic solvent | | | | | | |
| CH | 26.29 | (-) | 26.29 | (-) | 26.29 | (-) |
| Leveling agent | | | | | | |
| MEGAFAC R08 | 0.02 | 0.1 | 0.02 | 0.1 | 0.02 | 0.1 |
| Total | 100.0 | 100.0 | 100.0 | 100.0 | 100.0 | 100.0 |
| Evaluation item | | | | | | |
| Appropriate developing time(second) | | 20 | | 25 | | 25 |
| Resolution (line/space μm) | | 6 | | 6 | | 6 |
| Development latitude (μm) | | 6 | | 6 | | 8 |
| Appropriate developing time | | | | | | |
| Appropriate developing time + 30 seconds | | 50 | | 20 | | 50 |
| OD value (/μm) | | 5.1 | | 5.3 | | 5.3 |

As is evident from Table 1, each of the photosensitive compositions of Example 1 and 2 each using a thiol compound having a fluorene skeleton has high sensitivity that allows photo-curing even by a low exposure value of about 100 mj/cm² and is simultaneously excellent in development latitude compared with other thiol compounds. Therefore, the thiol compound and the photosensitive composition using the same of the present invention can be advantageously used in alkaline development type resists such as solder resists, etching resists and color filter resists.

As shown in Tables 4 to 5, the black matrix resist composition using the thiol compound having a fluorene skeleton of each of Examples 4 to 9 can be photo-cured even at a low exposure value of about 100 mj/cm² (high sensitivity) and is simultaneously excellent in development latitude compared with any other aliphatic thiol compound. Therefore, the black matrix resist composition containing the thiol compound having a fluorene skeleton of the present invention can be suitably used for a large-sized substrate.

INDUSTRIAL APPLICABILITY

The photosensitive composition using the novel thiol compound having a fluorene skeleton of the present invention has high sensitivity and excellent development latitude, so that it can be suitably used for etching resists, solder resists, color filter resists and the like, which form patterns in photolithography and alkaline development.

The photosensitive composition using the novel thiol compound having a fluorene skeleton of the present invention has high sensitivity and excellent development latitude, so that it can be suitably used for a large-sized color filter substrates.

The invention claimed is:

1. A photosensitive composition comprising: (A) a photopolymerization initiator system containing a thiol compound represented by formula (1):

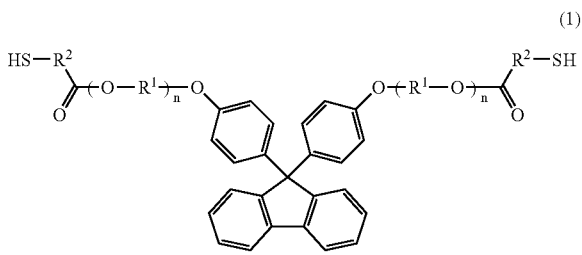

wherein $R^1$ represents a linear- or branched-chain alkylene group having 2 to 6 carbon atoms, $R^2$ is an alkylene group represented by the following formula (7) or (9):

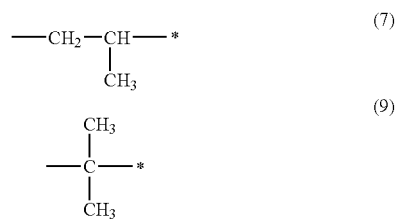

wherein * represents a binding site with a mercapto group, and n represents an integer of 1 to 4;

(B) a binder resin containing a carboxyl group; and (C) a compound having an ethylenically unsaturated group.

2. The photosensitive composition according to claim 1, in which the photopolymerization initiator system (A) contains a hexaarylbiimidazole compound and/or an aminoacetophenone compound.

3. The photosensitive composition according to claim 2, in which the hexaarylbiimidazole compound is represented by the following formula (14):

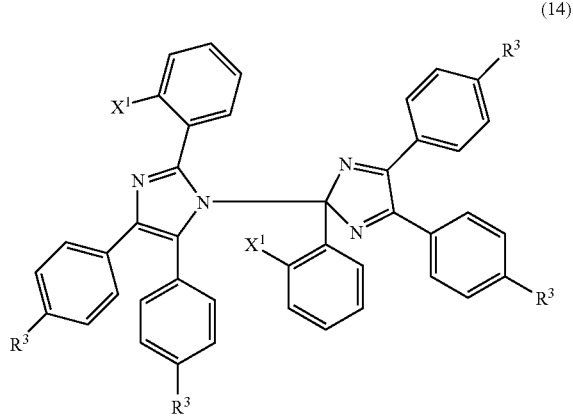

(14)

wherein $X^1$ represents a halogen atom and $R^3$ represents an alkyl group or an alkoxy group, which may have a substituent.

4. The photosensitive composition according to claim 1, in which the photopolymerization initiator system (A) contains a sensitizer.

5. The photosensitive composition according to claim 4, in which the sensitizer is one or more compounds selected from the group consisting of benzophenone-based compounds, thioxanthone-based compounds and ketocoumarin-based compounds.

6. The photosensitive composition according to claim 1, in which the binder resin containing a carboxyl group (B) further contains an ethylenically unsaturated group.

7. A black matrix resist composition for a color filter characterized by comprising: (A) a binder resin having a carboxyl group; (B) a compound having an ethylenically unsaturated group; (C) a photopolymerization initiator system containing a thiol compound represented by formula (1):

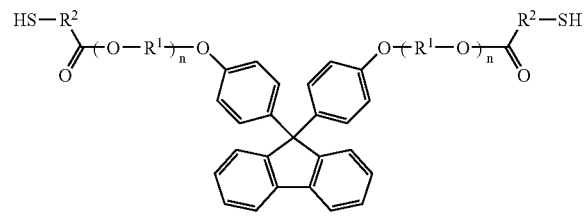

(1)

wherein $R^1$ represents a linear- or branched-chain alkylene group having 2 to 6 carbon atoms, $R^2$ is an alkylene group represented by the following formula (7) or (9):

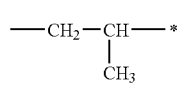

(7)

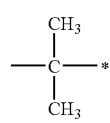

(9)

wherein * represents a binding site with a mercapto group, and n represents an integer of 1 to 4;
(D) a black pigment; and (E) an organic solvent.

8. The black matrix resist composition for a color filter according to claim 7, in which the binder resin (A) having a carboxyl group further contains an ethylenically unsaturated group.

9. The black matrix resist composition for a color filter according to claim 7, in which the binder resin (A) having a carboxyl group is a bisphenol-type epoxyacrylate resin.

10. The black matrix resist composition for a color filter according to claim 7, in which the photopolymerization initiator system (C) contains a hexaarylbiimidazole compound and/or an aminoacetophenone compound.

11. The black matrix resist composition for a color filter according to claim 10, in which the hexaarylbiimidazole compound is a compound represented by formula (14):

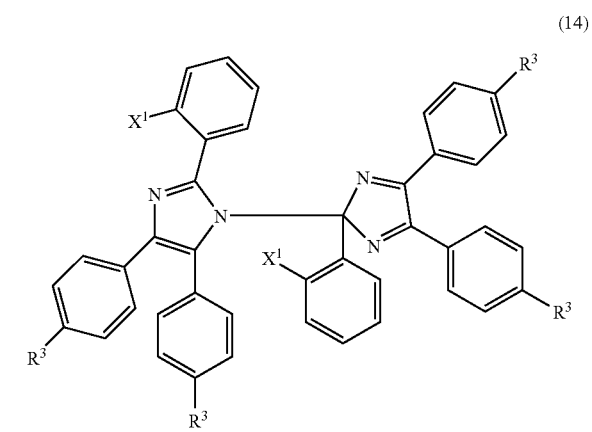

(14)

wherein $X^1$ represents a halogen atom, $R^3$ represents an alkyl group which may have a substituent or an alkoxy group which may have a substituent.

12. The black matrix resist composition for a color filter according to claim 10, in which the photopolymerization initiator system (C) further contains, as a sensitizer, one or more of compounds selected from the group consisting of a benzophenone-based compound, a thioxanthone-based compound, and a ketocoumarin-based compound.

13. The black matrix resist composition for a color filter according to claim 7, in which the black pigment (D) is carbon black and/or titanium black.

14. The black matrix resist composition for a color filter according to claim 7, in which each of the components except the organic solvent (E) is contained at a rate of content to the total mass of the respective components as follows:
(A) a binder resin having a carboxyl group: 10 to 30% by mass,
(B) a compound having an ethylenically unsaturated group: 2 to 20% by mass,
(C) a photopolymerization initiator system: 2 to 15% mass, and
(D) a black pigment: 40 to 80% by mass.

15. The black matrix resist composition for a color filter according to claim 14, in which the thiol compound of formula (1) is contained at 20 to 70% by mass in the photopolymerization initiator system (C).

* * * * *